(12) United States Patent
Almutairi et al.

(10) Patent No.: US 10,370,488 B2
(45) Date of Patent: Aug. 6, 2019

(54) STIMULUS-RESPONSIVE POLY(LACTIC-CO-GLYCOLIC)-BASED POLYMERS AND NANOPARTICLES FORMED THEREFROM

(71) Applicant: THE REGENTS OF THE UNIVERSITY OF CALIFORNIA, Oakland, CA (US)

(72) Inventors: Adah Almutairi, La Jolla, CA (US); Jason Olejniczak, San Diego, CA (US); Minnie Chan, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/564,693

(22) PCT Filed: Apr. 8, 2016

(86) PCT No.: PCT/US2016/026792
§ 371 (c)(1),
(2) Date: Oct. 5, 2017

(87) PCT Pub. No.: WO2016/164828
PCT Pub. Date: Oct. 13, 2016

(65) Prior Publication Data
US 2018/0079860 A1    Mar. 22, 2018

Related U.S. Application Data

(60) Provisional application No. 62/144,845, filed on Apr. 8, 2015.

(51) Int. Cl.
C08G 63/685 (2006.01)
A61K 9/51 (2006.01)
A61K 9/00 (2006.01)

(52) U.S. Cl.
CPC .......... *C08G 63/685* (2013.01); *A61K 9/0002* (2013.01); *A61K 9/5153* (2013.01)

(58) Field of Classification Search
CPC ... A61K 9/0002; A61K 9/5153; C08G 63/685
See application file for complete search history.

(56) References Cited

U.S. PATENT DOCUMENTS

| 8,828,383 B2 | 9/2014 | Almutairi et al. |
| 9,333,258 B2 | 5/2016 | Almutairi et al. |

(Continued)

FOREIGN PATENT DOCUMENTS

| EP | 2846872 A1 | 3/2015 |
| WO | 2011038117 A2 | 3/2011 |

(Continued)

OTHER PUBLICATIONS

Lux, C. et al. "Intramolecular Cyclization for Stimuli-Controlled Depolymerization of Polycaprolactone Particles Lading to Disassembly and Payload Release"; ACS Macro Lett, May 21, 2013; pp. 432-435, vol. 2(5).

(Continued)

*Primary Examiner* — Jianfeng Song
(74) *Attorney, Agent, or Firm* — Eleanor Musick; Musick Davison LLP

(57) ABSTRACT

PLGA-based polymers include pendant nucleophiles protected with photocleavable protecting groups. Upon deprotection, the polymers degrade rapidly via intramolecular cyclization into small molecules. The polymer may be formulated as a nanoparticle, with an encapsulated payload, which may be an imaging agent, a bioactive agent or a pharmaceutical agent.

19 Claims, 21 Drawing Sheets

SCHEME 1

(56) References Cited

U.S. PATENT DOCUMENTS

| | | |
|---|---|---|
| 9,333,259 B2 | 5/2016 | Almutairi et al. |
| 9,333,264 B2 | 5/2016 | Almutairi et al. |
| 9,409,322 B2 | 8/2016 | Almutairi et al. |
| 9,522,289 B2 | 12/2016 | Almutairi et al. |
| 9,700,620 B2 | 7/2017 | Almutairi et al. |
| 9,724,417 B2 | 8/2017 | Almutairi et al. |
| 10,188,461 B2 | 1/2019 | Almutairi et al. |
| 2013/0236500 A1 | 9/2013 | Zale et al. |
| 2015/0119792 A1 | 4/2015 | Almutairi et al. |
| 2015/0258195 A1 | 9/2015 | Almutairi et al. |

FOREIGN PATENT DOCUMENTS

| | | | |
|---|---|---|---|
| WO | 2011156666 A3 | 4/2012 | |
| WO | 2013169955 A1 | 11/2013 | |
| WO | WO-2013169953 A1 * | 11/2013 | ........... A61F 9/0008 |

OTHER PUBLICATIONS

Mahato, R., et al.; Biomaterials for Delivery and Targeting of Proteins and Nucleic Acides; CRC Press, (c) 2005, 57 pages, Sections 3.2.2 3.5, 4.1-4.42.

Olejniczak, J. et al,, Light Triggered Intramolecular Cyclization in Poly(lacticcoglycolic acid) Based Polymers for controlled Degradation; Macromolocules, 2015, pp. 3166-3172, vol. 48(10).

PCT/US2016/026792 International Search Report and Written Opinion dated Jul. 5, 2016, 5 pages.

\* cited by examiner

SCHEME 1

SCHEME 2

SCHEME 2 (Monomer 3)

SCHEME 2 (Monomer 8)

SCHEME 2 (Monomer 14)

SCHEME 3

SCHEME 4

STIMULUS-RESPONSIVE POLY(LACTIC-CO-GLYCOLIC)-BASED POLYMERS AND NANOPARTICLES FORMED THEREFROM

RELATED APPLICATIONS

This application is a '371 national stage filing of International Application No. PCT/US2016/026792, filed Apr. 8, 2016, which claims the benefit of the priority of U.S. Provisional Application No. 62/144,845, filed Apr. 8, 2015, each of which is incorporated herein by reference in its entirety.

GOVERNMENT RIGHTS

This invention was made with government support under Grant No. 1DP2OD006499-01 awarded by the National Institutes of Health. The government has certain rights in the invention.

FIELD OF THE INVENTION

The present invention relates polymers that rapidly degrade on demand, and more particularly to polymers incorporating sidechains that allow cyclization after removal of stimulus-responsive protecting groups.

BACKGROUND OF THE INVENTION

Stable polymers that depolymerize rapidly on demand upon application of a specific stimulus are of great interest for a variety of industrial applications, such as patterning, cosmetics, agriculture and electronics, and in biomedical applications such as tissue engineering, tissue adhesives, and drug delivery. Despite this interest, few synthetic polymers have been identified that have the ability to degrade with high sensitivity in response to specific stimuli. Most current degradable materials are unresponsive to the often subtle changes found in biological systems or, in the case of photodegradable polymers, require long, intense irradiation that may not be biologically compatible. The ongoing need for specifically engineered polymers is clearly seen in the broad use of unresponsive poly(lactic-co-glycolic acid) (PLGA) in current medical materials.

The emerging technology of nanoparticles packaging offers a way to package and deliver compounds of interest that offers a number of advantages. Nanoparticles can be synthesized and/or assembled so as to enclose other compounds of interest. Thus, nanoparticles can serve to protect compounds of interest by sequestration and/or encapsulation. Nanoparticulate media involved in this approach include nano- and microgels, nano- and microspheres, polymer micelles, and polymerized liposomes. Retention of the active compound in the nanocarriers is achieved by physical entrapment or by thermodynamic forces such as hydrophobic interactions.

Non-limiting examples of compounds of interest for delivery via nanoparticles to an area of interest, such as tumor tissue, include bioactive agents, pharmaceutical agents, or imaging agents. Nanoparticles may be then signaled to release their contents via externally-applied signals and/or signals present at the area of interest. In some examples, nanoparticles may be delivered systematically to a patient, while releasing of the contents of the nanoparticle at a focused area of interest within a living organism. Non-limiting examples of the contents of nanoparticles, i.e., payloads, include pharmaceutical agents, drugs, antibodies, and/or labeling compounds.

Nanoparticle packaging can also improve the effectiveness of bioactive agents and/or pharmaceutical agents. In some nanoparticle designs, the serum stability of bioactive agents and/or pharmaceutical agents can be enhanced and solubility limitations bypassed. Thus, nanoparticle packaging circumvents the vulnerability of bioactive agents and/or pharmaceutical agents, for example, to a reduction in efficacy due to bioavailability problems, e.g., solubility and/or stability. Moreover, such carriers can also serve to minimize undesirable side effects by reducing systemic exposure to drugs and/or by decreasing their necessary dosage. In addition, encapsulating bioactive agents and/or imaging agents may protect them from sequestration and/or renal clearance.

Nanoparticles also offer the potential, at least, for targeted delivery of their payloads to specific areas of interest within a patient. For example, an affinity reagent attached externally to nanoparticles enables an increase the concentration of such nanoparticles at their intended location. An example of such an affinity reagent is an antibody. Modifying the nanoparticles, and not the payload itself, avoids direct modification of the enclosed bioactive agent while improving its targeting and therefore obviates concerns about changing the activity of the bioactive agent.

Nanoparticles may be designed to be capable of a controlled and rapid triggered response to physiological events and/or conditions. Such physiological events and/or conditions may include changes in extracellular pH, temperature and reactive oxygen species. Therefore, nanoparticles capable of such a triggered response may be useful in the delivery of therapeutics and diagnostics to diseased cells and tissue. (See, e.g., Farokhzad, et al., (2006) Expert Opinion on Drug Delivery, 3, 311-324; Farokhzad & Langer (2009) ACS Nano, 3, 16-20: Ferrari, (2005) Nat. Rev. Cancer 5, 161-171; Ganta, et al., (2008) J. Control. Release, 126, 187-204; Langer (1990) Science, 249, 1527-33; LaVan, et al. (2003) Nat. Biotechnol. 21, 1184-1191; Whitesides (2003) Nat. Biotechnol. 21, 1161-1165; and Zhang et al. (2008) Clinical Pharmacology and Therapeutics, 83, 761-9).

Additionally, encapsulation within nanoparticles constructed from biodegradable polymers can allow bioactive agents to be delivered to the cytosol of diseased cells via endosomes and cytosolic release (Lewis (1990) Drugs and the Pharmaceutical Sciences, Vol. 45: Biodegradable Polymers as Drug Delivery Systems, Chasin & Langer, Eds.; Marcel Dekker, pp 1-42; Panyam & Labhasetwar (2003) Adv. Drug Delivery. Rev., 55, 329-347; and Shenoy, et al. (2005) Pharm. Res., 22, 2107-14.). Cytosolic delivery is particularly challenging and can be a major hurdle for effective therapeutic delivery (Vasir & Labhasetwar (2007) Adv. Drug Delivery. Rev., 59, 718-728; and Mescalchin et al. (2007) Expert Opin. Biol. Ther., 7, 1531-1538). Burst-degrading drug delivery systems hold promise in achieving increased cytosolic release through elevated osmotic pressure within the endosomes (Sonawane, et al. (2003) J. Biol. Chem. 2003, 278, 44826-31; and Hu, et al. (2007) Nano Lett. 7, 3056-64).

In the past, nanoparticles have been developed from hydrogels utilizing ketal crosslinks. However the payloads of such nanoparticles are usually limited to large water-soluble macromolecules. Unfortunately, with nanoparticles such as these, significant unwanted degradation occurs at physiological pH values over time (Cohen, et al. (2008) Bioconjug. Chem., 19, 876-81). Similarly, hydrophobic polyketals can encapsulate both hydrophobic and hydrophilic payloads, however, as nanoparticles they no longer undergo rapid acid catalyzed hydrolysis unless fully hydrated (Yang, et al. (2008) Bioconjug. Chem., 19, 1164-1169).

Formulation of nanoparticles from polymers may provide them with a hydrophobic character. However, this dramatically slows down their hydrolysis degradation kinetics as degradation only occurs slowly by a surface erosion mechanism (Heffernan, et al. (2009) Biomaterials, 30, 910-918; Heffernan & Murthy (2005) Bioconjug. Chem., 16, 1340-1342; Paramonov, et al. (2008) Bioconjug. Chem., 19, 911-919).

There is growing interest in polymeric biomaterials that can be remotely disassembled in a controlled fashion with an external stimulus, but are otherwise stable under physiological conditions (Wang, W.; Alexander, C. Angew. Chem. Int. Ed., 2008, 47, 7804-7806). Various internal and external stimuli, such as specific enzymes, temperature, ultrasound, and electromagnetic radiation, have been exploited as release mechanisms. (See, e.g., Veronese, et al. (2005) Bioconjugate Chem. 16, 775-784; Chung, et al. (1999) Controlled Release, 62 (1-2), 115-27; Liu, et al. (2005) Biomaterials, 26, 5064-5074; Na, et al. (2006) Eur. J. Pharm. Sci., 27, 115-122; Gao, et al. (2005) Controlled Release, 102, 203-22; Nelson, et al. (2002) Cancer Research, 62, 7280-83); and PCT Publication WO 2011/038117 A2, Almutairi et al.)

Nanoparticles composed of synthetic polymers such as poly(lactic-co-glycolic acid) (PLGA) are safe and attractive methods for DNA delivery applications and have been used in several studies. PLGA polyesters can be degraded by hydrolysis, facilitating their widespread use in medicine and biomedical research. Their dependence on slow hydrolysis makes for long degradation times (half-life of one year in vivo), thus limiting their applicability. While degradation can be sped up by copolymerization with more hydrophilic monomers; degradation is still too slow for triggered release or degradation.

Polylactide (PLA) and poly(D,L-lactide-co-glycolide) (PLGA) have been thoroughly investigated as drug delivery vehicles because of their slow hydrolytic degradation to largely biologically innocuous substances, but these polymers offer minimal control over degradation. Molecular engineering of the PLGA structures would accelerate degradation rates and allow triggered degradation.

SUMMARY OF THE INVENTION

In an exemplary embodiment, a series of polymers incorporating sidechains allow cyclization after removal of stimulus-responsive protecting groups such that exposure to the stimulus (e.g., light) would expose a pendant nucleophile to trigger intramolecular cyclization. This causes breaks in the polymer backbone and degradation into cyclic small molecules. The backbone itself will also degrade slowly via hydrolysis so that even with incomplete triggered degradation, the polymers still break down in an aqueous environment. These polymers add triggered degradation to the array of properties now found in the growing field of functional hydrolytically degradable PLGA-type polymers.

In one aspect of the invention, a novel polymeric structure is provided to enable rapid on-demand degradation and expand the library of polymers that degrade by cyclization. We have synthesized, by ring-opening polymerization (ROP), a series of PLGA-based polymers containing pendant nucleophiles protected with photocleavable protecting groups. Upon deprotection, of the polymers degrade rapidly via intramolecular cyclization into small molecules. Nanoparticles formulated from these polymers undergo rapid structural changes in response to UV light.

The inventive approach has been demonstrated with polymers bearing ortho-nitrobenzyl groups, yielding light-degradable polymers. $^1$H NMR spectra of model polymers of the same backbone were used to demonstrate degradation into cyclic small molecules, and fluorescence quenching of nanoparticle-encapsulated (by single emulsion) Nile red and dynamic light scattering confirmed light-triggered release and degradation of particles.

In one aspect of the invention, a composition comprises a polymer having a poly(lactide-co-glycolide)-type backbone and pendant nucleophiles protected by a stimulus-responsive protecting group, wherein the protecting group is configured to deprotect upon exposure to a stimulus to facilitate degradation by intramolecular cyclization. The protecting group may be photocleavable, where the stimulus may be UV light. In some embodiments, the protecting group is an ortho-nitrobenzyl (ONB) protecting group. The polymer may be formulated as a nanoparticle, and further comprise a payload encapsulated within the nanoparticle. The payload may be an imaging agent, a bioactive agent or a pharmaceutical agent. The pendant nucleophile may be an amine, an alcohol or a thiol.

In another aspect of the invention, a composition comprises a polymer comprising a polymer backbone comprising a poly(lactide-co-glycolide); and pendant nucleophiles linked to the backbone by photolabile protecting group, wherein the protecting group is configured to deprotect upon exposure to irradiation to facilitate degradation of the nucleophiles to five membered rings by intramolecular cyclization. In some embodiments, the irradiation is UV light. The protecting group is preferably an ortho-nitrobenzyl (ONB) protecting group. The polymer may be formulated as a nanoparticle, and further comprise a payload encapsulated within the nanoparticle. The payload may be an imaging agent, a bioactive agent or a pharmaceutical agent. The pendant nucleophile may be an amine, an alcohol or a thiol.

The inventive polymers have applications in on-demand and controlled drug delivery where the favorable properties of hydrophobic polyesters (processability and fabrication into particles, fibers, implants, etc.) can be combined with the favorable properties of hydrophilic polyesters (good biodegradation). Moreover, as the versatile design of this system allows easy replacement of the triggering group, the presented strategy may have a broad impact on polymer science.

DETAILED DESCRIPTION OF EXEMPLARY EMBODIMENTS

Figure 1A:
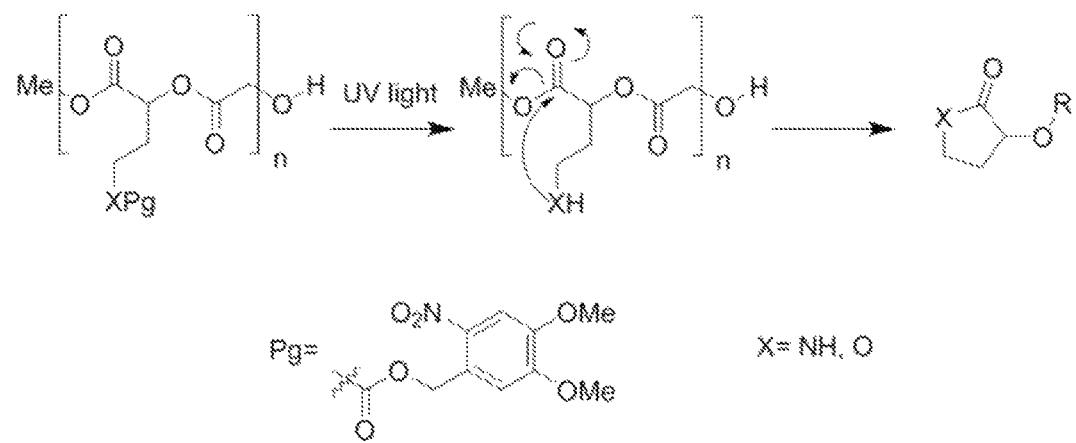
FIG. 1A shows the polymer degradation mechanism according to an embodiment of the invention.

According to embodiments of the invention, polymers incorporating sidechains allow cyclization after removal of stimulus-responsive protecting groups such that exposure to the stimulus (e.g., light) exposes a pendant nucleophile to trigger intramolecular cyclization. This causes breaks in the polymer backbone and degradation into cyclic small molecules. The backbone itself will also degrade slowly via hydrolysis so that even with incomplete triggered degradation, the polymers still break down in an aqueous environment. These polymers add triggered degradation to the array of properties now found in the growing field of functional hydrolytically degradable PLGA-type polymers.

Table 1 below provides a listing of abbreviations/acronyms and definitions used throughout the written description:

TABLE 1

| Abbreviation | Definition |
|---|---|
| AcOH | Acetic Acid |
| DLS | Dynamic light scattering |
| DMAP | 4-Dimethylaminopyridine |
| DMF | Dimethylformamide |
| GPC | Gel permeation chromatography |
| HRMS | High-resolution mass spectrometry |
| MeCN | Acetonitrile |
| NMR | Nuclear magnetic resonance |
| NP | Nanoparticle |
| ONB | ortho-nitrobenzyl |
| PBS | Phosphate Buffered Saline |
| PDI | Polydispersity Index |
| PLGA | Poly(lactic-co-glycolic acid) |
| PMMA | Poly(methyl methacrylate) |
| ppm | parts per million |
| ROP | ring-opening polymerization |
| TBAF | Tetra-n-butylammonium Fluoride |
| TBDPSCl | tert-Butyldiphenylchlorosilane |
| TEM | Transmission electron microscopy |
| TFA | Trifluoroacetic Acid |
| THF | tetrahydrofuran |
| UV | Ultraviolet |

In embodiments of the invention, polymers were designed to include (Scheme 1). An ortho-nitrobenzyl (ONB) protecting group, which degrades in response to UV light, was selected as the photocleavable moiety because this variety of protecting group is well-studied, commonly used in similar applications, and readily available. UV-degradable polymeric particles and other materials have been employed for biologically relevant purposes. These polymers add triggered degradation to the array of properties now found in the growing field of functional hydrolytically degradable poly (α-hydroxyl acid)s. The synthesis of the described polymers by a controlled ROP allows study of these novel backbones and shows their potential for direct use in degradable biomedical devices such as polymeric nanoparticles for drug delivery.

Polymeric nanoparticles composed of these polymers, when triggered, should rapidly degrade and release encapsulated molecules. Upon irradiation the component polymers immediately become more hydrophilic, allowing water into the particles, facilitating hydrolysis of the backbone, and would degrade rapidly by intramolecular cyclization. FIG. 1B diagrammatically illustrates the process for degradation of nanoparticles formulated from the polymers, where UV light triggers degradation into 5-membered rings and photocages encapsulating a payload, including, but not limited to, imaging agents, bioactive agents or pharmaceutical agents. The PLGA-based backbone also ensures complete degradation into small molecules through slower ester hydrolysis, facilitating their clearance, even without complete removal of pendant photocages.

Figure 1B:
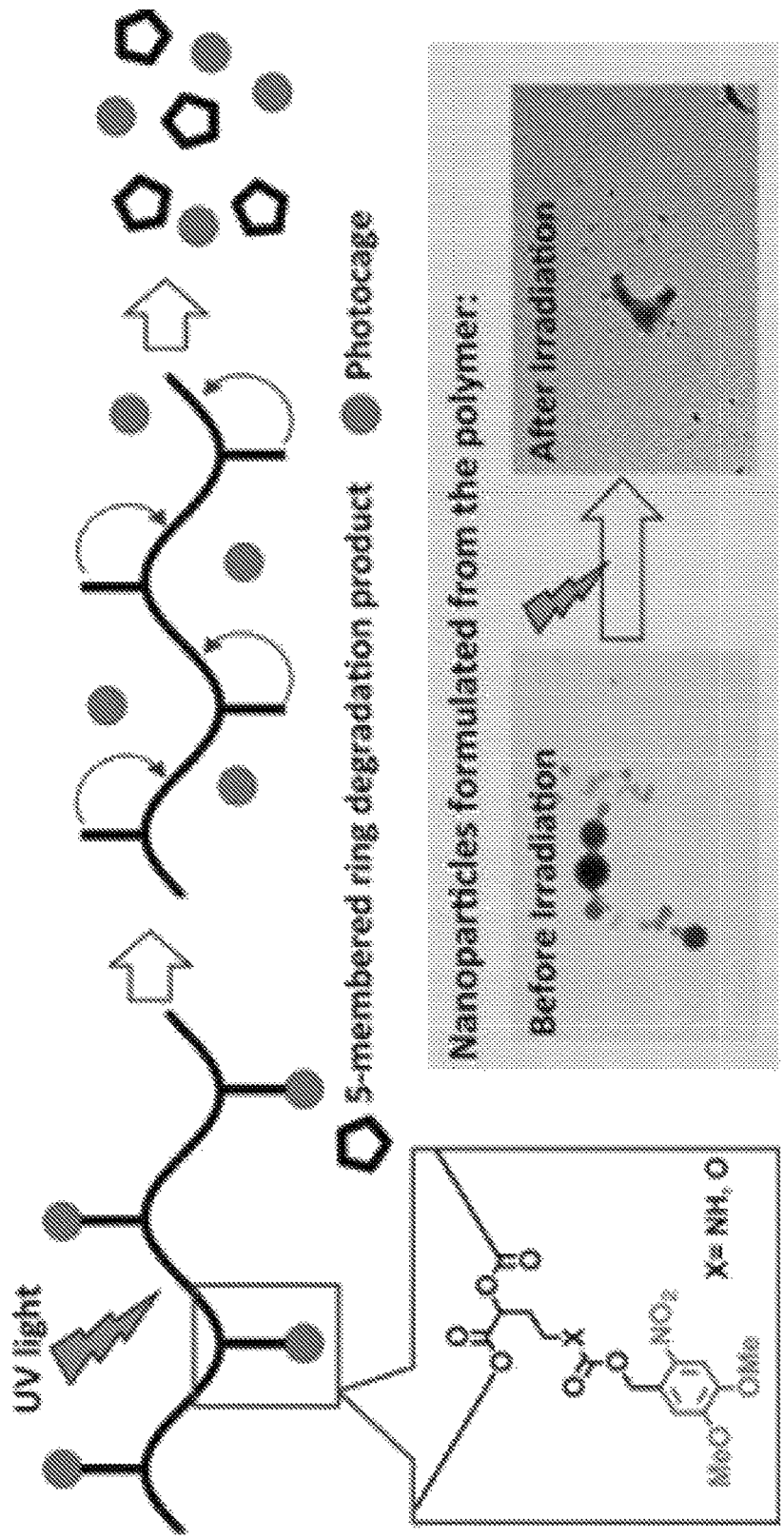
FIG. 1B is a diagram of the light-degradation process according to an embodiment of the invention.

Scheme 1, illustrated in FIG. 1A, shows the polymer degradation mechanism, where removal of the photolabile protecting group frees the pendant nucleophile to cleave the backbone ester and form a five membered ring.

All chemicals and solvents were purchased from Sigma-Aldrich (St. Louis, Mo.) and used as received unless otherwise specified. Compound 19, 1-[3,5-bis(trifluoromethyl) phenyl]-3-[(1R,2R)-(−)-2-(dimethylamino)cyclohexyl] thiourea (R,R-TUC), was purchased from Strem Chemicals (Newburyport, Mass.) and used as received. Anhydrous solvents were acquired from a solvent purification system (LC Technology Solutions, Inc. (Salisbury, Mass.), SP-1). Silica gel flash column chromatography was performed using an automated CombiFlash® Rf200 system. Polymer molecular weights and degradation were determined by gel permeation chromatography using a Waters e2695 instrument with a series of Styragel HR4 and Styragel HR2 columns in DMF with 0.01% LiBr at 37° C. Monodisperse PMMA standards were used to determine the molecular weight and PDI of polymers. $^1$H NMR and $^{13}$C NMR spectra were obtained using a Varian spectrometer working at 600 MHz and 150 MHz, respectively. Chemical shifts (δ) are reported in ppm relative to TMS, and coupling constants (J) are reported in Hertz. High-resolution mass spectra were acquired using an Agilent 6230 ESI-TOFMS in positive ion mode. Irradiation with UV light was done with a Luzchem LZ-ORG photoreactor equipped with 8 UV-A lamps with a power of 1.35 mW/cm$^2$ and a 0.181 W/cm$^2$, λex=320-90 nm, OmniCure S2000 Curing System. Particles were formulated using a Qsonica Sonicator 4000 and purified by tangential flow filtration using Millipore Pellicon XL, 500 kDa. Particles were characterized by DLS, Malvern Instruments Nanosizer, and scanning electron microscopy (TEM, Tenai Spirit). Fluorescence was measured using a Horiba Jobin FL-fluorimeter.

Three polymers with different pendant nucleophiles were synthesized: an amine, an alcohol, and a thiol. Preparation of a polymer series not only allows comparison of their degradation, but also examination of what chemistries are compatible with cyclization. Prior intramolecularly cyclizing polymers did not include alcohols as nucleophiles. Broadening the array of nucleophiles to include alcohols expands the types of chemistry that can be used to trigger degradation. Degradation by cyclization does not occur with analogous thiol nucleophiles in this series. Polymer properties were also compared in polymeric particles, which could be used for drug delivery or other applications.

The synthetic routes for the three monomers 3, 8 and 14 are shown in Scheme 2. The monomer with a pendant amine, monomer 3, was readily prepared from 1. The amine of 1 was first protected with the UV light-sensitive ortho-nitrobenzyl protecting group using triethylamine and compound 15. Alcohol 2 was then acylated with bromoacetyl bromide and subsequently cyclized with sodium bicarbonate to give dilactone 3 in a manner similar to that outlined by Pounder et al.

To obtain monomer 8 L-malic acid 4 was protected to form acetal 5 following an established procedure for D-malic acid. Acetal 5 was then reduced with borane to yield an alcohol that was immediately reacted with 4-nitrophenyl chloroformate to form carbonate 6. Carbonate 6 was reacted with 4,5-dimethoxy-2-nitrobenzyl alcohol to install the light-sensitive protecting group. The acetal was then hydrolyzed to reveal the vicinal alcohol and acid of 7. Compound 7 was cyclized to form the dilactone monomer 8 in a manner similar to that described for monomer 3.

Synthesis of monomer 14 required a distinct route because the ketal protecting group proved too labile under the conditions required to generate a thiol from compound 5. Instead, the protected thiol was formed by a more mild substitution reaction, a nucleophilic displacement of the bromine of compound 9 with sodium hydrosulfide, to yield thiol 10. Thiol 10 was protected with the ortho-nitrobenzyl protecting group using compound 15 to yield compound 11, the acetal of which was hydrolyzed to yield aldehyde 12. Aldehyde 12 was treated with trimethyl silyl cyanide and zinc iodide to yield a cyanohydrin which was then hydrolyzed to afford acid 13. Compound 13 was reacted with bromoacetyl bromide in the same manner as the previous two monomers to afford dilactone monomer 14.

Figure 2A:
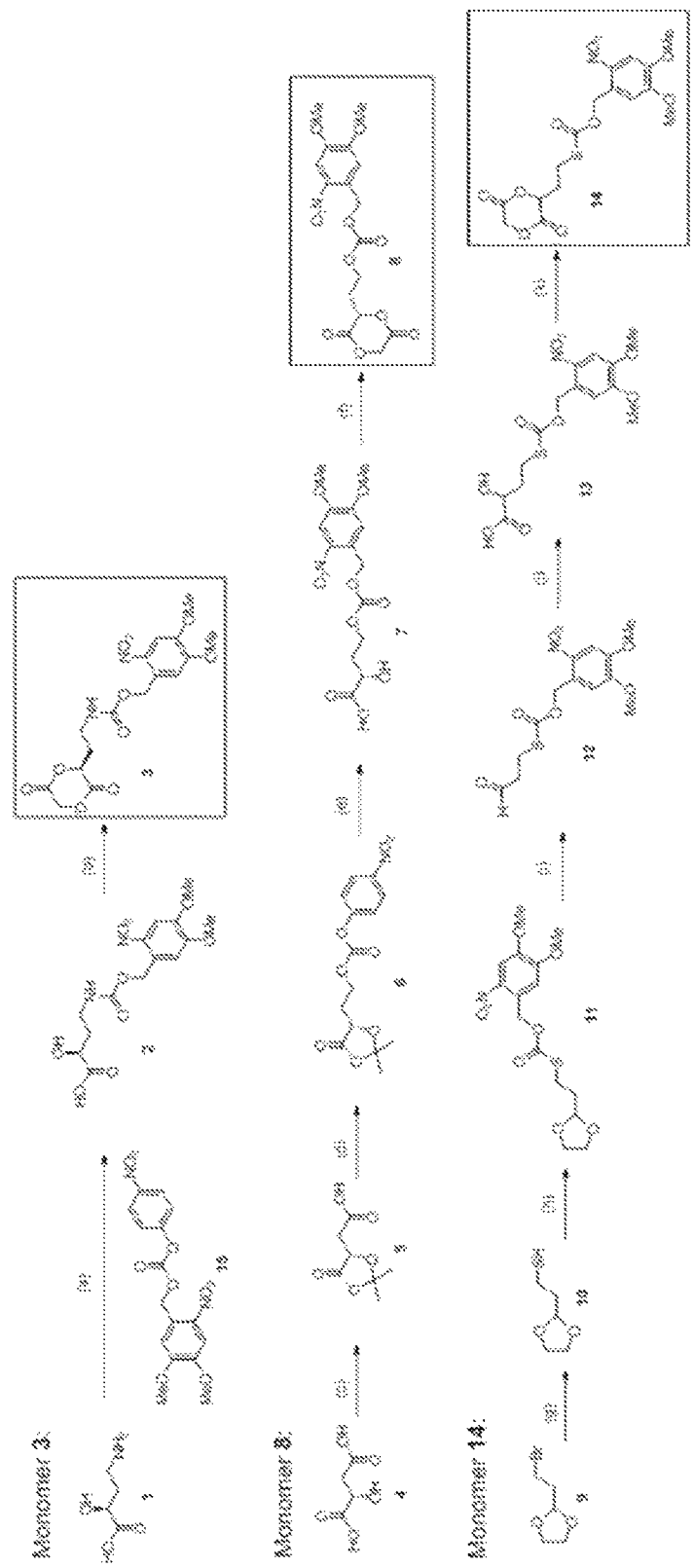
FIG. 2A shows the synthesis of three monomers (3, 8 and 14) according to one embodiment of the invention (Scheme 2)

Scheme 2, illustrated in FIG. 2A, shows the synthesis of monomers with reagents and conditions: a) 15, Et$_3$N, MeCN, reflux, 61%; b) (i) bromoacetyl bromide, Et$_3$N, MeCN, 0° C.; (ii) NaHCO$_3$, DMF, 45% over two steps, c) p-toluenesulfonic acid, 2,2-dimethoxypropane, CH$_2$Cl$_2$, 95%; d) (i) borane, THF 0° C.; (ii) 4-nitrophenyl chloroformate, pyridine, CH$_2$Cl$_2$, 0° C., 48% over two steps; e) (i) 4,5-dimethoxy-2-nitrobenzyl alcohol, DMAP, pyridine, CH$_2$Cl$_2$, 0° C., 68%; (ii) THF, H$_2$O, AcOH, 100%; f) (i) bromoacetyl bromide, Et$_3$N, MeCN, 0° C.; (ii) DMF, NaHCO$_3$, 58% over two steps. g) Sodium hydrosulfide, DMF, 0° C., 80%; h) 15, pyridine, DMAP, CH$_2$Cl$_2$, 0° C., 85%; i) THF, 1M HCl, 98%; j) (i) Trimethylsilyl cyanide, ZnI$_2$, CH$_2$Cl$_2$, 0° C., 98%; (ii) HCl (Concentrated), 1,4-Dioxane, 50° C., 59%; k) (i) bromoacetyl bromide, Et$_3$N, MeCN 0° C.; (ii) DMF, NaHCO$_3$, 41% over two steps.

Figure 2B:
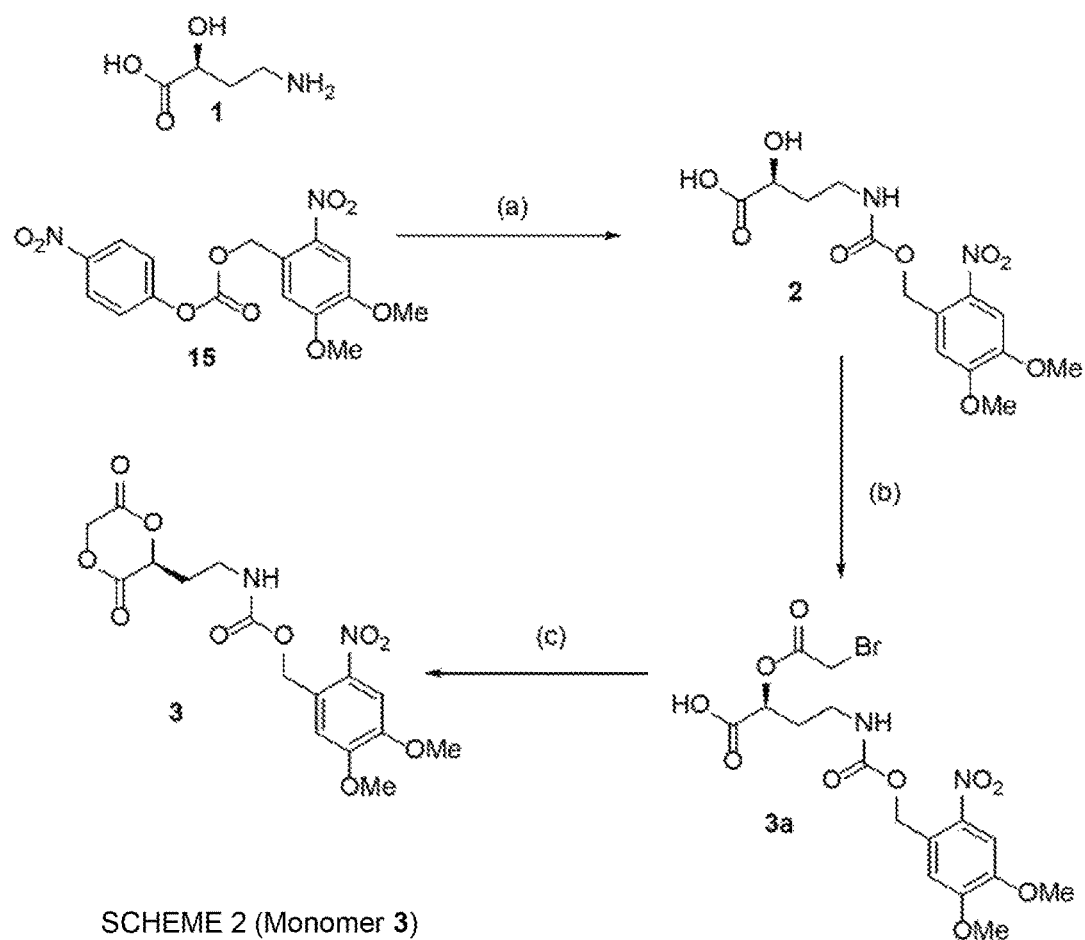
FIGS. 2B-2D show synthesis of monomers 3, 8 and 14, respectively, with added detail.
Figure 2C:
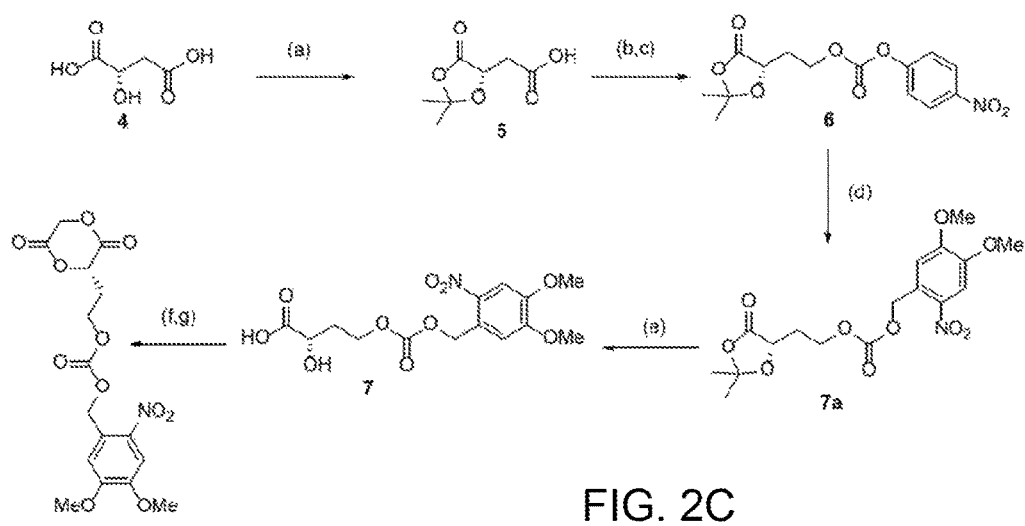
Figure 2D:
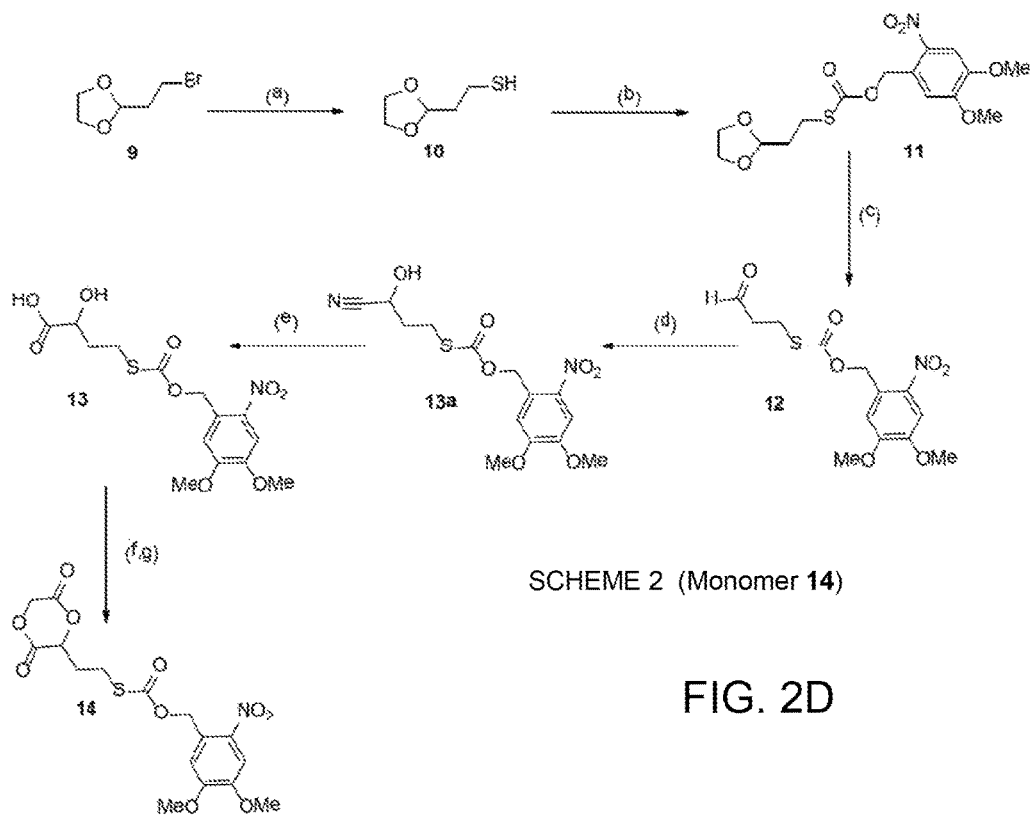

FIGS. 2B-2D provide additional details for synthesis of monomers 3, 8, and 14. Referring to FIG. 2B (monomer 3), for compound 2, compound 1 (1.70 g, 14.3 mmol) and compound 15 (4.153 g, 10.93 mmol) were suspended in MeCN (170 mL). Et$_3$N (6.1 mL, 43.8 mmol) was added dropwise to the suspension. The reaction mixture was heated at reflux for 18 h. The reaction mixture was concentrated and purified by silica column (1:1 MeOH/EtOAc) to yield compound 2 as a yellow solid (2.38 g, 61%).

High-resolution mass spectrometry (HRMS) was used to determine composition of compound 2: $C_{14}H_{19}N_2O_9$; measured mass 358.1087; theoretical mass: 358.1085.

NMR Results: $^1$H NMR (600 MHz, CDCl$_3$) δ 7.67 (s, 1H), 6.99 (s, 1H), 5.76-5.66 (bs, 1H) 5.46 (s, 2H), 4.21-4.15 (m, 1H), 3.97 (s, 3H), 3.93 (s, 4H), 3.48-3.32 (m, 2H), 2.12-1.98 (m, 1H), 1.91-1.80 (m, 1H). $^{13}$C NMR (151 MHz, CDCl$_3$) δ 162.9, 156.5, 153.8, 148.1, 139.6, 128.5, 110.1, 108.1, 63.6, 56.6, 56.5, 38.2, 36.7, 34.1.

For compound 3a, compound 2 (900 mg, 2.51 mmol) was dissolved in MeCN (18 mL) and was chilled to 0° C. Et$_3$N (0.39 mL, 2.76 mmol) was added dropwise. A solution of bromoacetyl bromide (0.24 mL, 2.76 mmol) in MeCN (9 mL) was added dropwise to the chilled solution of compound 3. The reaction was quenched after 1 hour of stirring by adding 1 M HCl. The reaction mixture was extracted three times with ethyl acetate the combined organic was washed with brine, dried over MgSO$_4$ and was concentrated. The resulting orange oil was used in the next step without further purification.

Compound 3: Compound 3a (2.51 mmol), used without purification, was dissolved in DMF (37.5 mL) and dripped into a suspension of NaHCO$_3$ (316 mg, 3.76 mmol) in DMF (75 mL) over a period of 28 hours. The reaction was stirred for a further 8 hours. The reaction mixture was filtered and concentrated. The resulting oil was purified by silica column (1:3 Hex/EtOAc) to yield compound 3 as a yellow solid (450 mg, 45%) over two steps.

Using HRMS, composition was $C_{16}H_{18}N_2O_{10}Na$; measured mass 421.0856; theoretical mass: 421.0854.

NMR results: $^1$H NMR (600 MHz, CDCl$_3$) δ 7.69 (s, 1H), 6.99 (s, 1H), 5.49 (d, J=14.4 Hz, 1H), 5.47 (d, J=14.4 Hz, 1H), 5.15-5.08 (m, 2H), 4.95 (d, J=16.2 Hz, 1H), 4.91 (d, J=16.2 Hz, 1H), 3.99 (s, 3H), 3.96 (d, J=12.4 Hz, 3H), 3.55-3.41 (m, 2H), 2.42 (m, 1H), 2.20 (m, 1H). $^{13}$C NMR (151 MHz, CDCl$_3$) δ 165.8, 164.2, 156.3, 148.5, 140.2, 127.5, 111.0, 108.4, 100.1, 73.6, 65.7, 64.1, 56.7, 56.6, 36.7, 31.2.

Referring to FIG. 2C, compound 5 was synthesized from compound 4, L-malic acid, via a previously-described method using D-malic acid.

For compound 6, compound 5 (929 mg, 5.3 mmol) was dissolved in THF (6 mL) in base washed glassware. The solution was chilled to 0° C. and a 1 M solution of borane in THF (8 mL) was added dropwise over 30 min. The reaction was allowed to warm to room temperature gradually and allowed to react for 3.5 h. The reaction mixture was quenched with methanol at −78° C. and was concentrated. The reaction mixture was dissolved once more in methanol and concentrated, then dissolved in ethyl acetate and concentrated a final time. The reaction mixture was dissolved in $CH_2Cl_2$ (8 mL) without purification. The solution was chilled to 0° C. and pyridine (1.401 mL, 17.4 mmol) was dripped in. A solution of 4-nitrophenyl chloroformate (2.338 g, 11.6 mmol) in $CH_2Cl_2$ (12 mL) was slowly dripped into the reaction mixture. The mixture was allowed to warm to room temperature and react for 12 hours. The reaction was quenched with distilled water, organic collected and aqueous extracted 2× more with $CH_2Cl_2$. The combined organic was washed with brine, dried over $MgSO_4$, and concentrated. Purified by silica column ($CH_2Cl_2$) to yield compound 6 as colorless oil (0.900 g, 47.7%) HRMS: composition: $C_{14}H_{15}NO_8Na$; measured mass 348.0689; theoretical mass: 348.0690.

NMR results for compound 6: $^1H$ NMR (600 MHz, $CDCl_3$) δ 8.31-8.26 (m, 2H), 7.41-7.37 (m, 2H), 4.56 (dd, J=7.0, 4.8 Hz, 1H), 4.54-4.49 (m, 1H), 4.48-4.43 (m, 1H), 2.38-2.31 (m, 1H), 2.29-2.21 (m, 1H), 1.65 (s, 3H), 1.58 (s, 3H). $^{13}C$ NMR (151 MHz, $CDCl_3$) δ 172.6, 155.5, 152.3, 145.5, 125.4, 122.0, 111.2, 70.8, 64.7, 30.4, 27.1, 25.8.

Still referring to FIG. 2C, for compound 7a, 4,5-dimethoxy-2-nitrobenzyl alcohol (1.096 g, 5.15 mmol) and DMAP (62.9 mg, 0.515 mmol) were dissolved in $CH_2Cl_2$ (11 mL) and chilled to 0° C. Pyridine (0.83 mL, 10.3 mmol) was dripped into the solution. A solution of compound 6 (1.676 g, 5.15 mmol) in DCM (13 mL) was added to the reaction mixture. The reaction mixture was warmed to room temperature and allowed to react for 16 hours. The reaction mixture was quenched with saturated $NaHCO_3$ solution and was extracted 3× with $CH_2Cl_2$, the combined organic was washed with brine, dried over $MgSO_4$, then concentrated. Purified by silica column ($CH_2Cl_2$) to yield compound 7a as yellow solid (1.392 g, 67.6%).

Using HRMS, the composition was determined to be $C_{17}H_{21}NO_{10}Na$; measured mass was 422.1055; theoretical mass: 422.1058.

NMR results for compound 7a: $^1H$ NMR (600 MHz, $CDCl_3$) δ 7.73 (s, 1H), 7.10 (s, 1H), 5.62 (d, J=14.4 Hz, 1H), 5.58 (d, J=14.4 Hz, 1H), 4.52 (dd, J=6.9, 4.8 Hz, 1H), 4.45-4.34 (m, 2H), 4.02 (s, 3H), 3.96 (s, 3H), 2.32-2.24 (m, 1H), 2.23-2.14 (m, 1H), 1.62 (s, 3H), 1.56 (s, 3H). $^{13}C$ NMR (151 MHz, $CDCl_3$) δ 172.7, 154.4, 153.8, 148.3, 139.6, 126.8, 111.0, 109.9, 108.1, 70.8, 66.4, 63.6, 56.7, 56.4, 30.6, 27.1, 25.8.

For compound 7, compound 7a (1.827 g, 4.57 mmol) was dissolved in $THF/H_2O/AcOH$ 1:1:1 (19 mL), the mixture was stirred for 118 hrs. The reaction mixture was concentrated then dissolved in $CH_2Cl_2$. The $CH_2Cl_2$ was washed one time with 1 M HCl. The aqueous was extracted twice with $CH_2Cl_2$. The combined organic was dried over $MgSO_4$ and concentrated to yield compound 7 as a yellow oil (1.64 g, 100%). Using HRMS, composition was $C_4H_{17}NO_{10}Na$. Measured mass was 382.0744; theoretical mass: 382.0745.

NMR analysis results for compound 7: $^1H$ NMR (600 MHz, $CDCl_3$) δ 7.70 (s, 1H), 7.03 (s, 1H), 5.56 (s, 2H), 4.44-4.33 (m, 3H), 3.97 (s, 3H), 3.95 (s, 3H), 2.30-2.20 (m, 1H), 2.12-2.03 (m, 1H). $^{13}C$ NMR (151 MHz, $CDCl_3$) δ 177.9, 154.9, 153.9, 148.5, 139.8, 126.5, 110.4, 108.3, 67.1, 66.7, 64.3, 56.7, 56.5, 33.0.

For compound 8, compound 7 (1.487 g, 4.14 mmol) was dissolved in acetonitrile (28 mL) and chilled to 0° C. $Et_3N$ (0.635 mL, 4.55 mmol) was dripped in followed by the dropwise addition of a solution of bromoacetyl bromide (0.918 g, 4.55 mmol) in MeCN (14 mL). The reaction was quenched with 1 M HCl, and extracted 3× with ethyl acetate. The combined organic was dried over $MgSO_4$ and concentrated. The resulting orange oil was used without further purification. The oil was dissolved in DMF (63 mL) and dripped into a suspension of $NaHCO_3$ (521 mg, 6.21 mmol) in DMF (126 mL) over a period of 28 hours. The reaction was stirred for a further 8 hours. The reaction mixture was concentrated, then suspended in ethyl acetate. The suspension was filtered and the filtrate was collected and concentrated. The resulting oil was purified by silica column (1:1 Hex/EtOAc) then recrystallized ($CH_2Cl_2$/Ether) to yield compound 8 as a yellow solid (0.952 g, 57.7%) over two steps.

NMR analysis results for compound 8: $^1H$ NMR (600 MHz, $CDCl_3$) δ 7.73 (s, 1H), 7.05 (s, 1H), 5.60 (d, J=14.4 Hz, 1H), 5.57 (d, J=14.4 Hz, 1H), 5.11 (dd, J=7.8, 4.2 Hz, 1H), 5.00 (d, J=16.2 Hz. 1H), 4.94 (d, J=−16.2 Hz, 1H), 4.49-4.42 (m, 2H), 4.01 (s, 3H), 3.97 (s, 3H), 2.61-2.53 (m, 1H), 2.40-2.34 (m, 1H). $^{13}C$ NMR (151 MHz, $CDCl_3$) δ 165.4, 163.8, 154.5, 153.8, 148.7, 126.1, 110.8, 108.4, 100.1, 72.1, 67.0, 66.7, 62.8, 56.8, 56.6, 30.21.

Referring now to FIG. 2D, synthesis of monomer 14 begins with compound 10, sodium hydrosulfide (2.477 g, 44.2 mmol), which was dissolved in DMF and chilled to 0° C. Compound 9 (2.59 mL, 22.1 mmol) was dripped in and the reaction was allowed to warm to room temperature and stirred 20 h. The reaction was quenched by adding water. The reaction mixture was extracted 4× with hexanes, after which the combined organic was dried over $MgSO_4$ and concentrated to yield compound 10 (2.384 g, 80.4%) as a colorless oil.

NMR analysis results for compound 10: $^1H$ NMR (600 MHz, $CDCl_3$) δ 4.96 (t, J=4.5 Hz, 1H), 4.00-3.92 (m, 2H), 3.90-3.81 (m, 2H), 2.64 (q, J=15.1, 7.8 Hz, 2H), 1.99 (dt, J=10.2, 4.2 Hz, 2H), 1.48 (t, J=7.8 Hz, 1H). $^{13}C$ NMR (151 MHz, $CDCl_3$) δ 103.1, 65.1, 38.2, 19.2.

For compound 11, a suspension of compound 10 (4.225 g, 11.2 mmol) and DMAP (0.136 g, 1.1 mmol) was prepared in $CH_2Cl_2$ (24 mL) and chilled to 0° C. Pyridine (1.799 g, 22.4 mmol) was dripped into the suspension. Compound 15 (1.5 g, 11.17 mmol) was dissolved in $CH_2Cl_2$ (15 mL) and dripped into the suspension. The suspension was allowed to come to room temperature and react for 16 hours, by which time all material was in solution. The reaction was quenched by diluting with $CH_2Cl_2$ then washing with 1 M HCl, deionized water, saturated sodium carbonate twice, and finally one wash with brine. The organic layer was dried over $MgSO_4$ and concentrated. The resulting oil was purified by silica column ($CH_2Cl_2$/MeOH 9:1) to yield compound 11 as a yellow solid (3.554 g, 85.2%).

NMR analysis results for compound 11: $^1H$ NMR (600 MHz, $CDCl_3$) δ 7.73 (s, 1H), 7.00 (s, 1H), 5.67 (s, 2H), 4.96 (t, J=4.3 Hz, 1H), 4.00-3.94 (m, 8H), 3.90-3.83 (m, 2H), 3.04-2.99 (m, 2H), 2.08-2.01 (m, 2H). $^{13}C$ NMR (151 MHz, $CDCl_3$) δ 170.8, 153.9, 148.4, 139.7, 127.1, 109.9, 108.3, 102.9, 65.7, 65.6, 65.2, 56.6, 56.5, 34.0, 25.6.

For compound 12, compound 11 (2 g, 5.3 mmol) was dissolved in a 1:1 mixture of THF and 1 M HCl (40 mL). The reaction mixture was stirred for 5 days. The reaction mix was diluted with deionized water and extracted 3× with CH$_2$Cl$_2$. The combined organic was dried over MgSO$_4$ and concentrated to yield Compound 12 (1.702 g, 97.8%) as a yellow oil.

HRMS analysis identified the composition: C$_{13}$H$_{15}$NO$_7$SNa. Measured mass was 352.0460; theoretical mass: 352.0461.

NMR analysis results for compound 12: $^1$H NMR (600 MHz, CDCl$_3$) δ 9.78 (s, 1H), 7.73 (s, 1H), 6.98 (s, 1H), 5.67 (s, 2H), 3.99 (s, 3H), 3.96 (s, 3H), 3.14 (t, J=6.6 Hz, 2H), 2.92 (t, J=6.6 Hz, 2H). $^{13}$C NMR (151 MHz, CDCl$_3$) δ 199.6, 170.6, 153.9, 148.5, 139.8, 126.7, 110.0, 108.4, 66.9, 56.7, 56.6, 44.1, 23.6.

For compound 13a, compound 15 (1.302 g, 3.95 mmol) and zinc iodide were dissolved in CH$_2$Cl$_2$ and chilled to 0° C. Trimethylsilyl cyanide (0.989 mL, 7.91 mmol) was dripped in and the reaction was allowed to proceed for 1 hour. The reaction was then diluted with CH$_2$Cl$_2$ and washed 3× with saturated NaHCO$_3$ solution. The organic layer was dried over MgSO$_4$ and concentrated to yield compound 13a (1.656 g, 97.7%) as a yellow oil.

NMR analysis results for compound 12: $^1$H NMR (600 MHz, CDCl$_3$) δ 7.73 (s, 1H), 6.98 (s, 1H), 5.68 (d, J=14.4 Hz, 1H), 5.64 (d, J=14.4 Hz, 1H), 4.54 (dd, J=7.8, 5.4 Hz, 1H), 3.99 (s, 3H), 3.95 (s, 3H), 3.11-3.02 (m, 1H), 3.02-2.94 (m, 1H), 2.26-2.10 (m, 2H), 0.218 (s, 9H). $^{13}$C NMR (151 MHz, CDCl$_3$) δ 170.2, 153.8, 148.6, 126.4, 119.4, 110.3, 108.4, 100.1, 66.0, 59.8, 56.6, 56.5, 36.2, 26.2, −0.3.

For compound 13, compound 13a (1.656 g, 3.864 mmol) was dissolved in a 1:1 mixture of 1,4-dioxane and concentrated HCl (8 mL). The reaction mixture was heated at 50° C. for 15 hours. The mixture was cooled to room temperature and diluted with distilled water. The reaction mixture was extracted 3× with CH$_2$Cl$_2$. The combined organic was dried over MgSO$_4$ then concentrated. The resulting yellow oil was purified by C18 column (H$_2$O/MeCN, 3:2) to yield compound 13 (0.8618 g, 59.4%).

HRMS analysis identified the composition: C$_{14}$H$_{17}$NO$_9$SNa. Measured mass was 398.0521; theoretical mass: 398.0516.

NMR analysis results for compound 13: $^1$H NMR (600 MHz, CDCl$_3$) δ 7.73 (s, 1H), 6.99 (s, 1H), 5.71-5.64 (m, 2H), 4.41-4.30 (m, 1H), 4.00 (s, 3H), 3.96 (s, 3H), 3.15-3.03 (m, 2H), 2.29-2.19 (m, 1H), 2.13-2.03 (m, 1H).

For compound 14, compound 13 (0.823 g, 2.19 mmol) was dissolved in MeCN (14 mL) and chilled to 0° C. Et$_3$N (0.398 mL, 2.85 mmol) after which a solution of bromoacetyl bromide (0.2489 mL, 2.85 mmol) in acetonitrile (7 mL) was dripped in over 10 min. The reaction mixture was diluted with EtOAc then washed 3× with lM HCl. The organic layer was dried over MgSO$_4$ and concentrated. The resulting orange oil was used without further purification. The oil was dissolved in DMF (33 mL) and dripped into a suspension of NaHCO$_3$ (276 mg, 3.29 mmol) in DMF (66 mL) over a period of 28 hours. The reaction was stirred for a further 8 hours. The reaction mixture was concentrated, then suspended in ethyl acetate. The suspension was filtered and the filtrate was collected and concentrated. The resulting oil was purified by silica column (1:1 Hex/EtOAc) to yield compound 14 as a yellow solid (0.373 g, 41.0%) over two steps.

NMR analysis results for compound 14: $^1$H NMR (600 MHz, CDCl$_3$) δ 7.73 (s, 1H), 6.98 (s, 1H), 5.68 (d, J=14.4 Hz, 1H), 5.64 (d, J=14.4 Hz, 1H), 4.54 (dd, J=7.8, 5.4 Hz, 1H), 3.99 (s, 3H), 3.95 (s, 3H), 3.11-3.02 (m, 1H), 3.02-2.94 (m, 1H), 2.26-2.10 (m, 2H), 0.218 (s, 9H). $^1$H NMR (600 MHz, CDCl$_3$) δ 7.72 (s, 1H), 6.98 (s, 1H), 5.70-5.60 (m, 2H), 5.10-5.05 (m, 1H), 4.99 (d, J=16.8 Hz, 1H), 4.94-4.88 (d, J=16.8 Hz, 1H), 3.99 (s, 3H), 3.96 (s, 3H), 3.21-3.13 (m, 1H), 3.10-3.03 (m, 1H), 2.54-2.46 (m, 1H), 2.40-2.31 (m, 1H). $^{13}$C NMR (151 MHz, CDCl$_3$) δ 170.1, 166.4, 164.1, 153.8, 148.7, 126.2, 110.7, 108.5, 100.1, 73.6, 66.21, 66.6, 56.7, 56.0, 31.1, 26.2.

Figure 3:
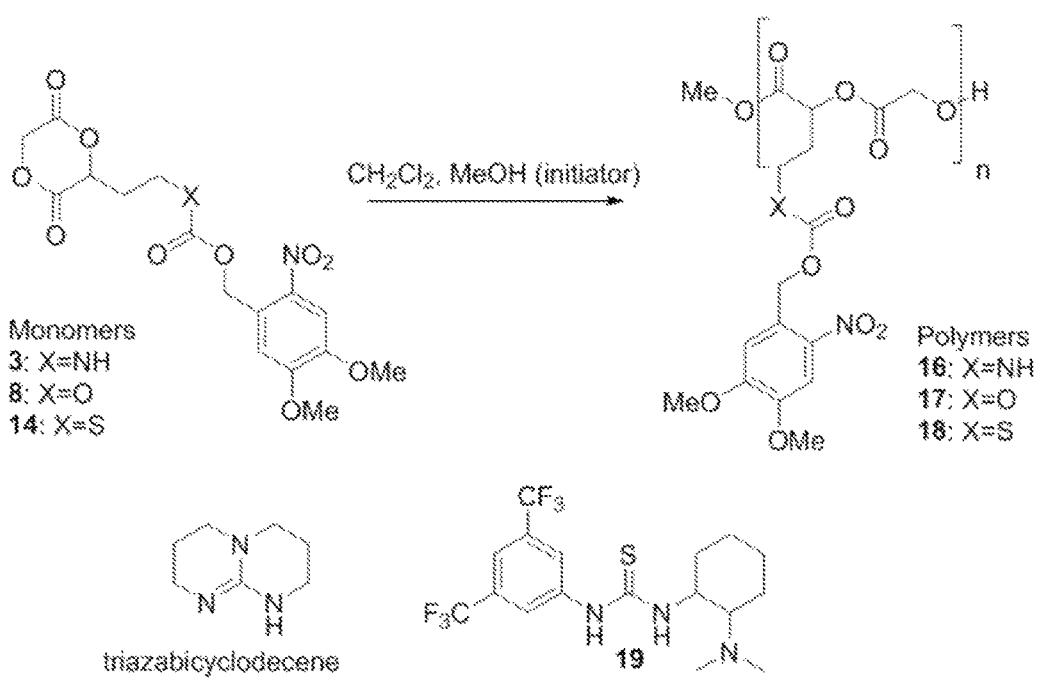
FIG. 3 shows preparation of three exemplary light-degradable polymers (polymers 16, 17 and 18) according to another embodiment of the invention (Scheme 3).

Scheme 3, illustrated in FIG. 3, shows the preparation of the three light-degradable polymers 16, 17, and 18: Triazabicyclodecene was used as catalyst and 19 was used as co-catalyst.

The three monomers were polymerized by organic-catalyzed ring-opening polymerization (ROP). We could not directly follow the method used by Dove et al. for this variety of monomer due to commercial unavailability of the catalyst (−)-sparteine. Instead, an alternative reported organocatalyst, triazabicyclodecene, was selected for ROP (Scheme 3). Commercially available compound 19, 1-[3,5-bis(trifluoromethyl)phenyl]-3-[(1R,2R)-(−)-2-(dimethylamino) cyclohexyl]thiourea (R,R-TUC), was also included as a co-catalyst. The triazabicyclodecene alone was sufficient to catalyze ROP, but at a much slower rate. Attempts at polymerization with metal catalysts were unsuccessful because of poor solubility in compatible solvents and the high melting points of the monomers in bulk. Weight-average molecular weights (MW) of the polymers were determined by gel permeation chromatography (GPC) relative to PMMA standards to be 3,800 Da (PDI=1.2) for polymer 16, 19,200 Da (PDI=1.5) for polymer 17, and 12,200 Da (PDI=1.5) for polymer 18 using PMMA standards. Side reactions during ROP were a limiting factor in MW for the polymers. Polymer 16's length appeared to be limited by side reactions like transcarbamation.

The synthesis of polymers 16, 17 and 18 was performed as follows:

Polymer 16: Compound 3 (141 mg, 0.35 mmol) and compound 19 (26 mg, 0.063 mg) were suspended in CH$_2$Cl$_2$ (1.5 mL). 125 μL of 0.1 M methanol in CH$_2$Cl$_2$ were added dropwise to the reaction mixture. 125 μL of 0.1 M triazabicyclo[4.4.0]dec-5-ene in CH$_2$Cl$_2$ were added dropwise to the reaction mixture. The suspended compound 3 cleared as the reaction proceeded. The reaction was allowed to proceed for 24 hours. The polymer was purified by repeated precipitation into cold hexanes from a CH$_2$Cl$_2$ solution to yield Polymer 16 (85 mg, 85%) as a yellow solid.

Polymer 17: Compound 8 (141 mg, 0.35 mmol) and compound 19 (18 mg, 0.044 mmol) were dissolved in CH$_2$Cl$_2$ (1.5 mL). 89 μL of 0.1 M methanol in CH$_2$Cl$_2$ were added dropwise to the reaction mixture. 89 μL of 0.1 M triazabicyclo[4.4.0]dec-5-ene in CH$_2$Cl$_2$ were added dropwise to the reaction mixture. The reaction was allowed to proceed for 15 hours. The polymer was purified by repeated precipitation into cold ether from a CH$_2$Cl$_2$ solution to yield Polymer 17 (141 mg, 100%) as a yellow solid.

Polymer 18: Compound 14 (103 mg, 0.25 mmol) and compound 19 (13 mg, 0.031 mmol) were dissolved in CH$_2$Cl$_2$ (1.5 mL). 62 μL of 0.1 M methanol in CH$_2$Cl$_2$ were added dropwise to the reaction mixture. 62 μL of 0.1 M triazabicyclo[4.4.0]dec-5-ene in CH$_2$Cl$_2$ were added dropwise to the reaction mixture. The reaction was allowed to proceed for 20 hours. The polymer was purified by repeated precipitation into cold ether from a CH$_2$Cl$_2$ solution to yield Polymer 18 (91 mg, 89%) as a yellow solid.

NMR analysis results were $^1$H NMR (600 MHz, CDCl$_3$) δ 7.69 (s, 1H), 6.98 (s, 1H), 5.62 (s, 2H), 5.28 (s, 1H), 4.98-4.62 (m, 2H), 3.98 (s, 3H), 3.94 (s, 3H), 3.01 (s, 2H), 2.32 (s, 2H).

Figure 4A:
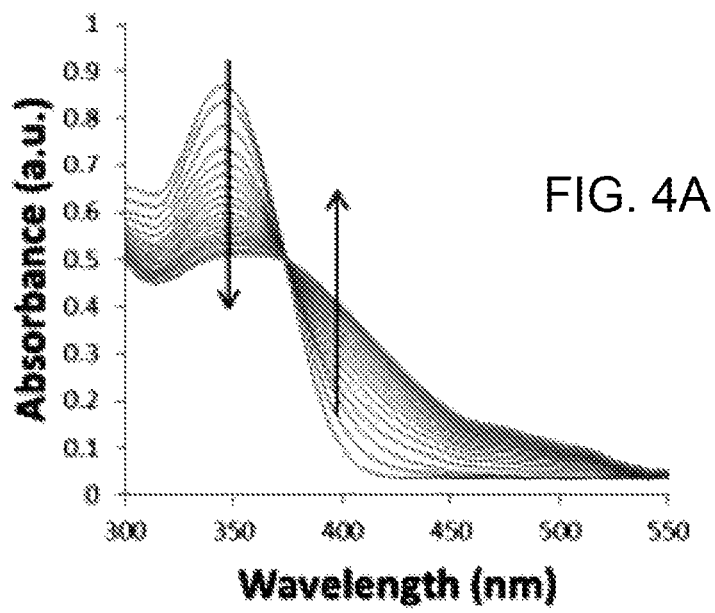
FIGS. 4A-4C are UV absorbance spectra upon irradiation with UV light of polymer 16, polymer 17, and polymer 18, respectively, with a spectrum recorded at 0 minutes and each minute thereafter for 18 minutes total.
Figure 4B:
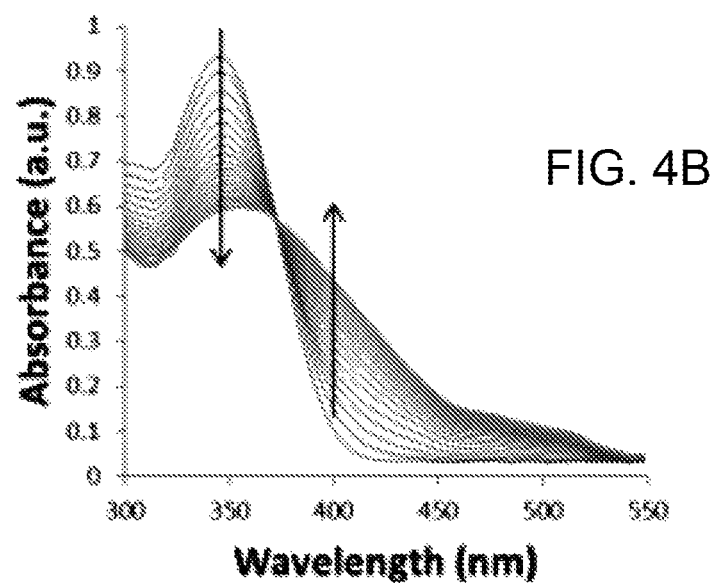
Figure 4C:
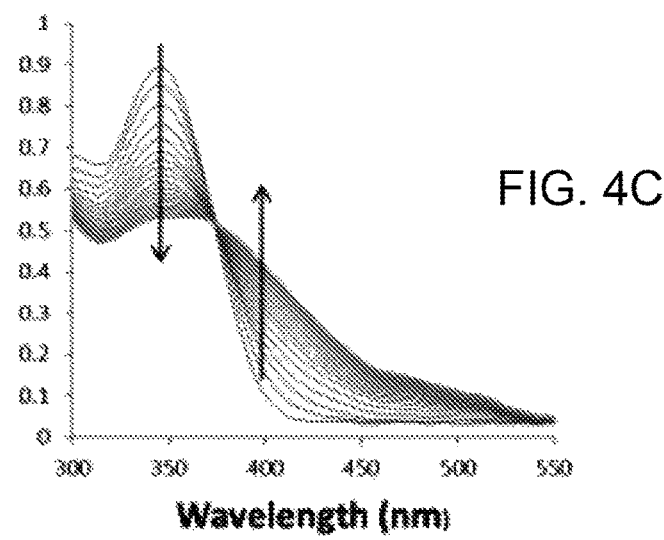
Figure 4D:
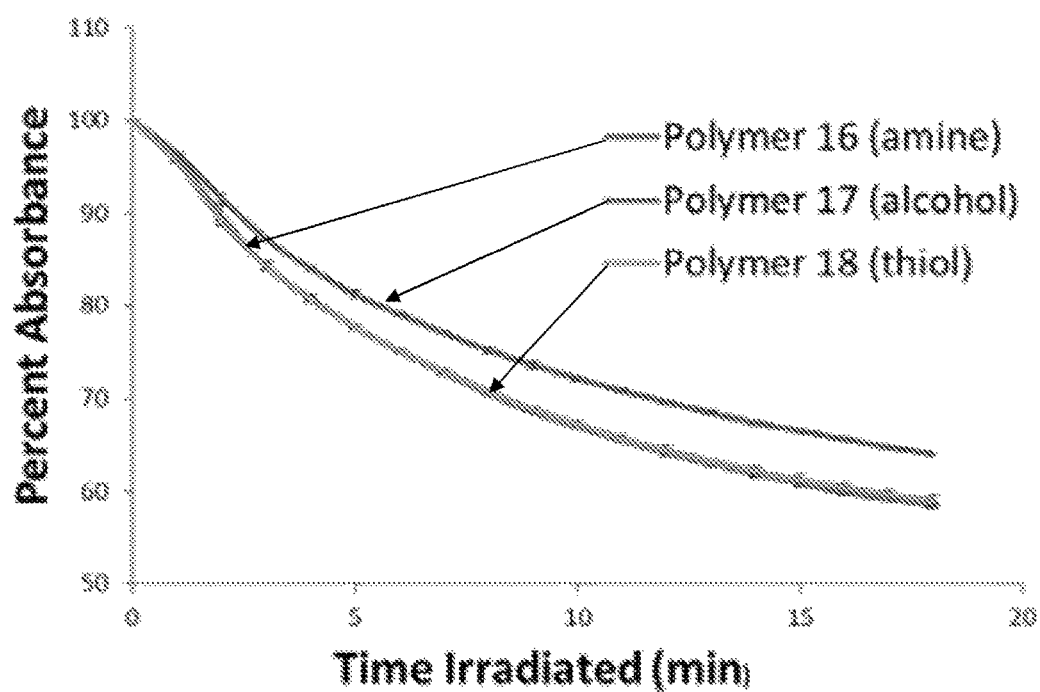
FIG. 4D is a plot showing the change in absorbance at 346 nm upon irradiation for the three polymers.

To characterize the polymer degradation, we first compared the sensitivities of the carbamate, carbonate, and thiocarbonate photocleavable protecting groups of the polymers 16, 17, and 18 respectively. Polymers were irradiated with UV light (1 mW/cm$^2$) for the specified times up to 18 min and the change in absorbance at 346 nm was monitored. The peak at 346 nm, corresponding to the 4,5-dimethoxy-2-nitrobenzyl protecting group decreased, while a new peak at 400 nm, associated with the cleaved 4,5-dimethoxy-2-nitrosobenzaldehyde, formed (FIGS. 4A-4C). The percent absorbance was plotted over time (FIG. 4D). The three protecting groups are quite similar in sensitivity, though the carbonate protecting group of polymer 17 is slightly less sensitive than the other two.

Figure 5A:
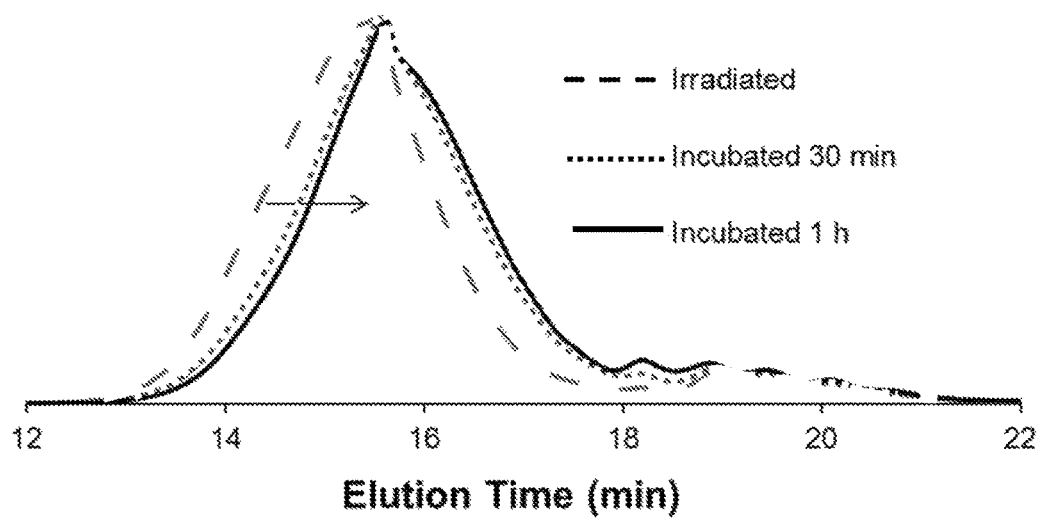
FIGS. 5A and 5B show GPC traces of polymer 17 and polymer 18, respectively, following 15 min irradiation (1 mW/cm$^2$) and subsequent incubation for the specified times at 37° C. The irradiation was relatively brief for this concentration so the cyclization chemistry could be readily observed.
Figure 5B:
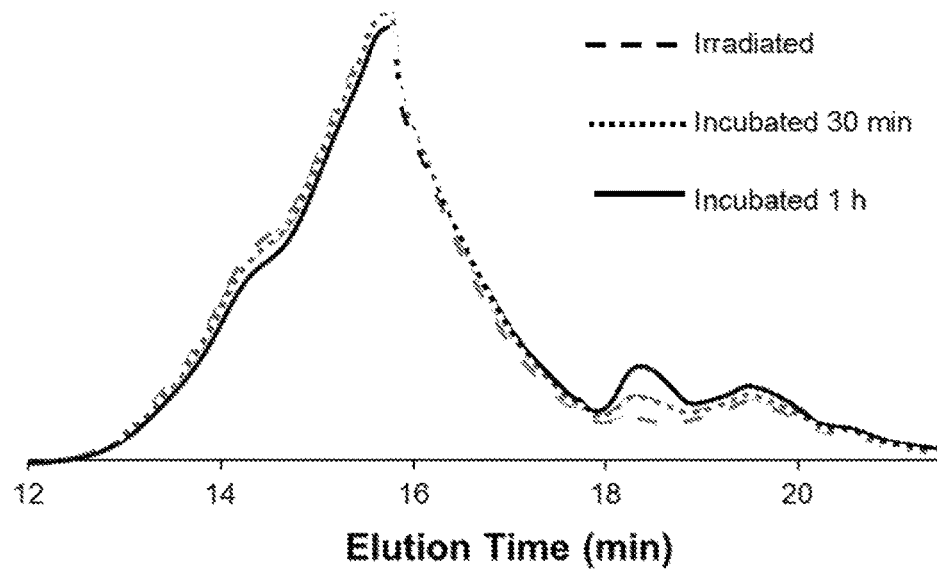

FIGS. 5A and 5B are GPC traces of a) polymer 17 and b) polymer 18 following 15 min irradiation (1 mW/cm$^2$) and subsequent incubation for the specified times at 37° C. The irradiation was relatively brief for this concentration so the cyclization chemistry could be readily observed.

Figure 6A:
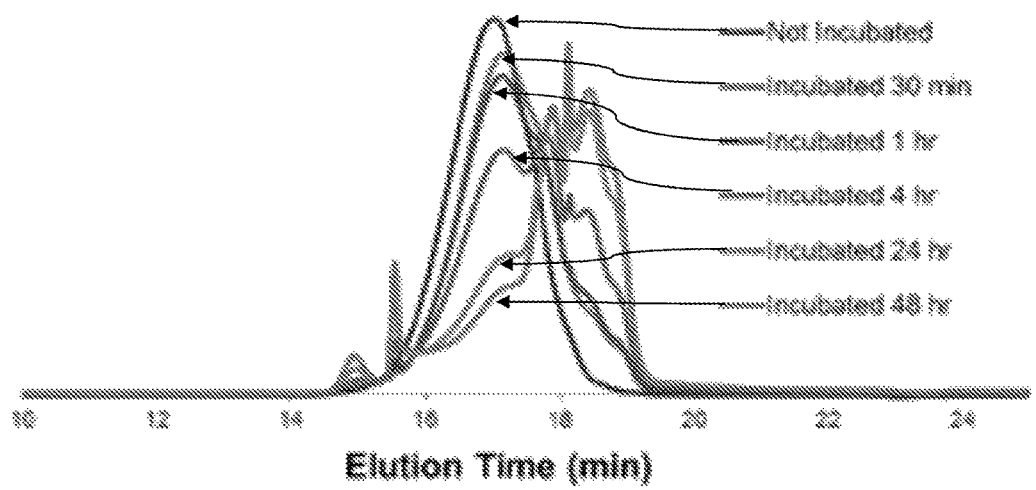
FIGS. 6A-C are GPC traces for polymer 16, polymer 17 and polymer 18, respectively, without irradiation.
Figure 6B:
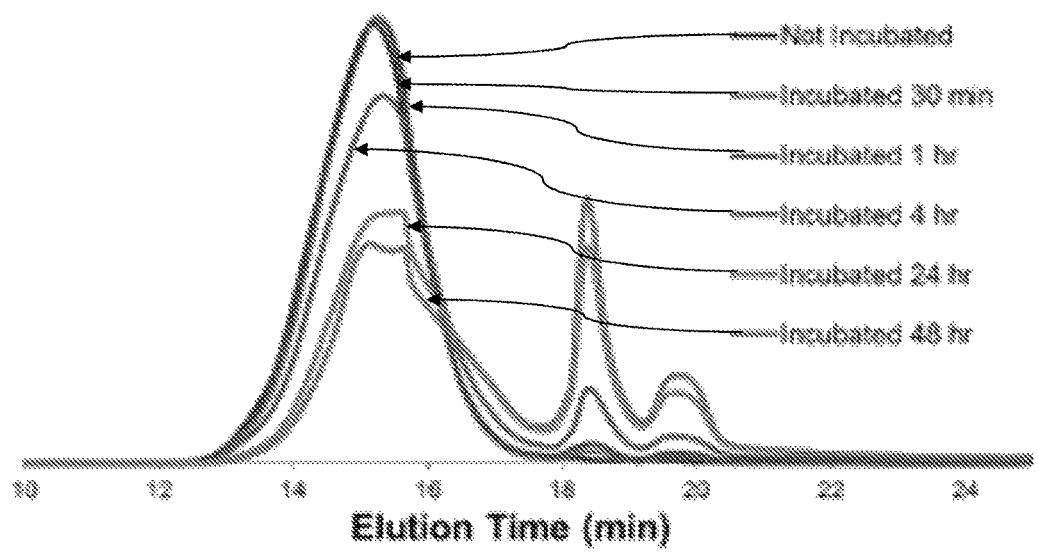
Figure 6C:
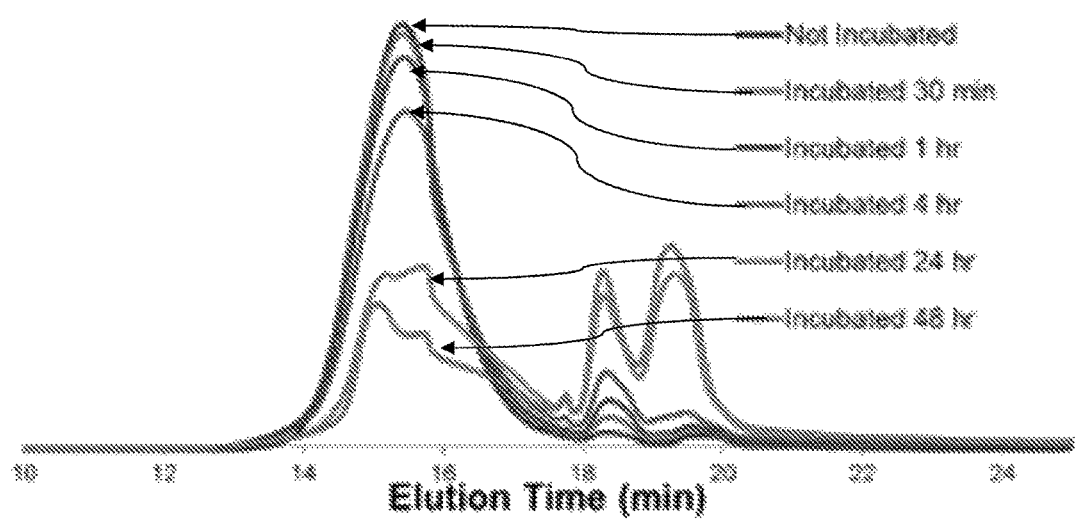
Figure 7A:
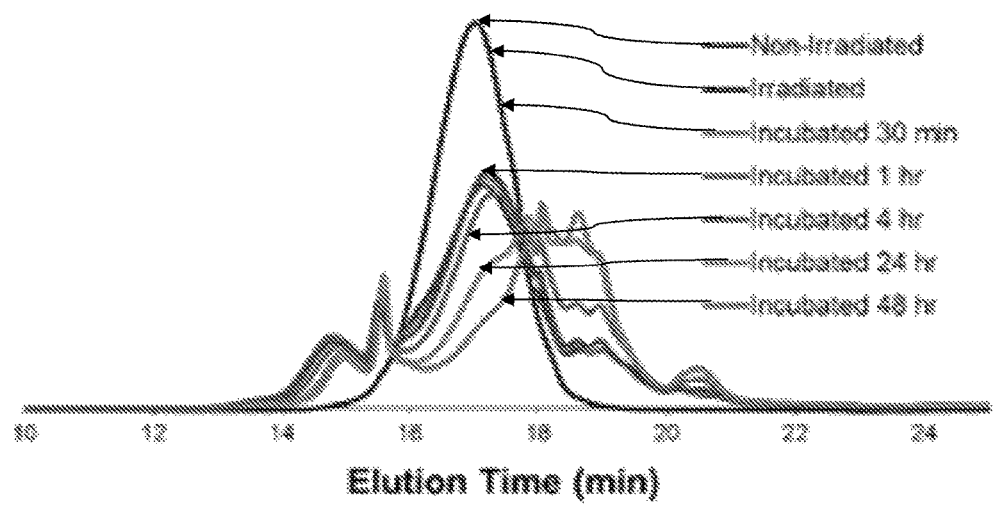
FIGS. 7A-C are GPC traces for polymer 16, polymer 17 and polymer 18, respectively, following 15 min. irradiation.
Figure 7B:
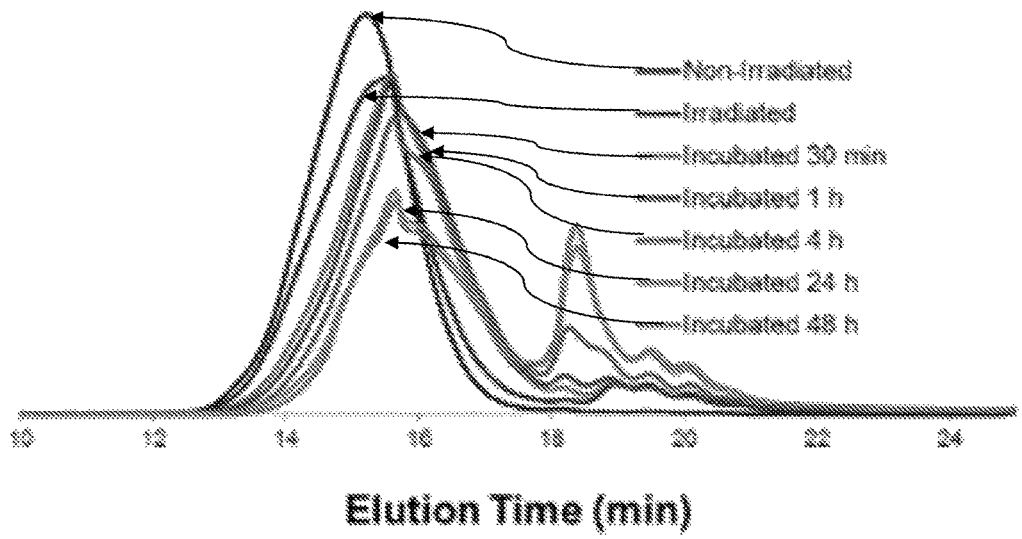
Figure 7C:
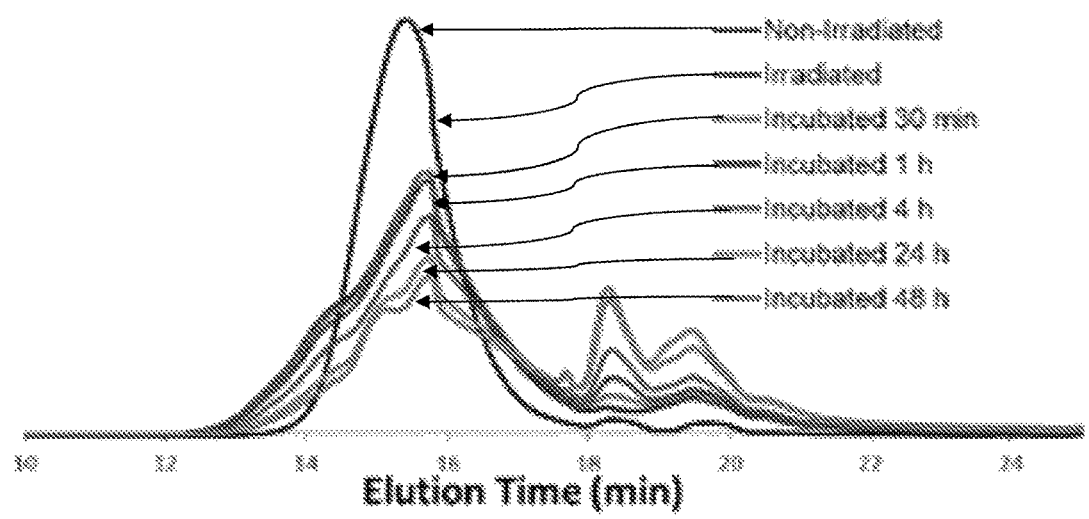

Polymer degradation was monitored by gel permeation chromatography. Each polymer was dissolved in 9:1 acetonitrile/phosphate buffer pH 7.4 and irradiated for 15 min (1 mW/cm$^2$), then incubated at 37° C. for specified times before concentrating the samples and analyzing by GPC. The 15 min of irradiation at this concentration is only enough to cleave a minor percentage of the protecting groups. This avoided substantial changes in the polarities of polymers 17 and 18. Even with the low level of irradiation used polymer 16 underwent a substantial change in polarity, causing unfavorable interactions with the GPC columns that impeded interpretation (FIGS. 6A-C). Polymer 17 was amenable to GPC following irradiation; the initial irradiated trace (dashed line) shifted to longer elution times following incubation for 30 min (dotted line) and 1 hour (solid line) (FIG. 5A). This indicates a shift to lower molecular weight fragments, consistent with intramolecular cyclization. The minor difference between the 30 min. and 1 hr. traces suggests that the intramolecular cyclization reactions of polymer 17 are quite rapid, largely completing within 30 min of incubation. The molecular weight of polymer 18 did not change in 1 hr. (FIG. 5B). Changes did not occur until after 4 hours of incubation, as can be seen in FIG. 7B. As this amount of time is compatible with hydrolysis of exposed thiocarbonate protecting groups (FIG. 5B), we infer that this structure did not cyclize appreciably at this temperature and the apparent degradation was unrelated to breaking of the polymer backbone. This result is not surprising, as the cyclization would necessitate an enthalpically unfavorable conversion of an ester to a thioester, though the reaction would be entropically favorable at higher (less biologically relevant) temperatures.

Figure 8:
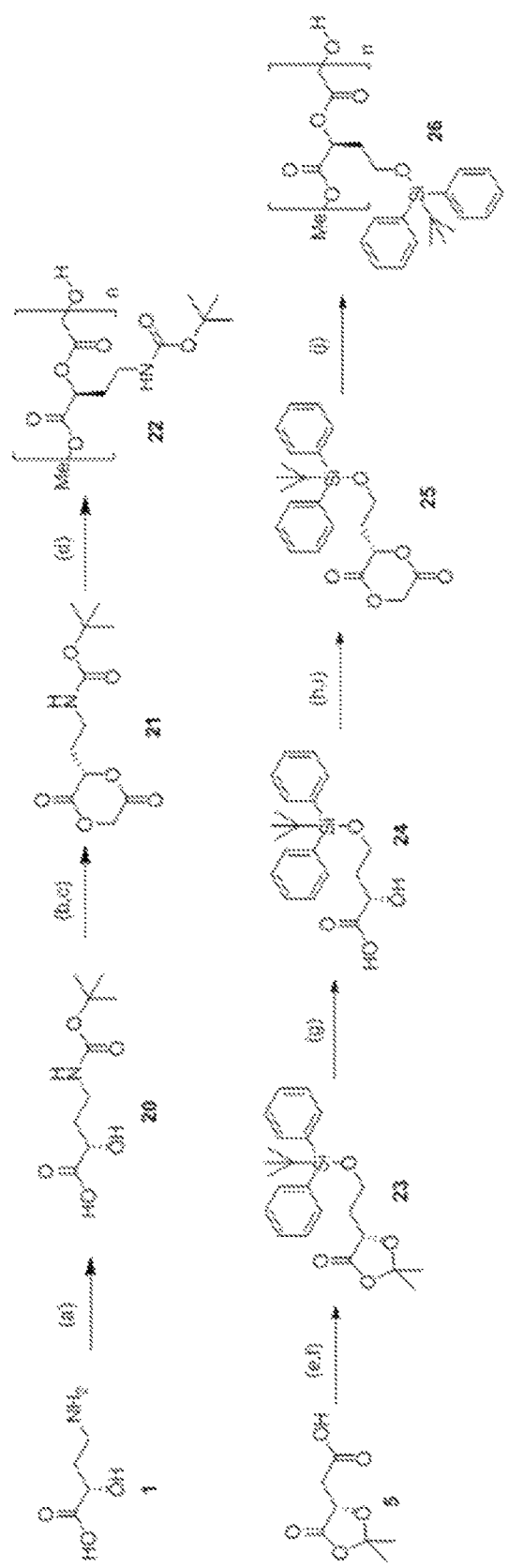
FIG. 8 shows the synthesis of the model polymer in an embodiment of the invention (Scheme 4).

Scheme 4, shown in FIG. 8, illustrates the synthesis of the model polymers using the following reagents and conditions: (a) Boc$_2$O, K$_2$CO$_3$, H$_2$O, dioxane; (b) bromoacetyl bromide, Et$_3$N, MeCN, 0° C.; and (c) DMF, NaHCO$_3$, 25% over two steps; (d) Sn(Oct)$_2$, 125° C., 29%. Synthesis of the silyl-protected model polymer; (e) borane, THF, 0° C.; and (f) TBDPSCl, pyridine, CH$_2$Cl$_2$, 59% over two steps; (g) THF, H$_2$O, AcOH, 73%; (h) bromoacetyl bromide, Et$_3$N, MeCN, 0° C.; and (i) DMF, NaHCO$_3$, 15% over two steps; (j) 19, MeOH, triazabicyclo[4.4.0]dec-5-ene, CH$_2$Cl$_2$, 48%.

In Scheme 4, compounds 20-21 and Polymer 22 were synthesized as follows:

Compound 20: Compound 20 was synthesized from compound 1, (S)-(−)-4-Amino-2-hydroxybutyric acid, via a previously described method.

Compound 21: Compound 20 (2.758 g, 12.59 mmol) was dissolved in acetonitrile (91 mL) and chilled to 0° C. Et$_3$N (2.28 mL, 16.37 mmol) was dripped in followed by the dropwise addition of a solution of bromoacetyl bromide (1.43 mL, 16.37 mmol) in MeCN (30 mL). The reaction was stirred for 1.25 hour. The reaction was quenched with 1 M HCl, and extracted 3× with ethyl acetate. The combined organic was dried over MgSO$_4$ and concentrated. The resulting oil was used without further purification. The oil was dissolved in DMF (190 mL) and was dripped into a suspension of NaHCO$_3$ (1.586 g, 18.89 mmol) in DMF (381 mL) over a period of 28 hours. The reaction was stirred for a further 8 hours. The reaction mixture was concentrated then suspended in ethyl acetate. The suspension was filtered and the filtrate was collected and concentrated. The resulting oil was purified by silica column (1:1 Hex/EtOAc) then recrystallized (CH$_2$Cl$_2$/Ether) to yield compound 20 as colorless crystals (0.808 g, 24.7%) over two steps.

HRMS analysis was used to determine the composition, which was: C$_{11}$H$_{17}$NO$_6$Na. Measured mass was 282.0946; theoretical mass: 282.0948.

NMR results for compound 21 were: $^1$H NMR (600 MHz, CDCl$_3$) δ 5.03 (dd, J=7.8, 4.8 Hz, 1H), 4.95 (d, J=16.2 Hz, 1H), 4.91 (d, J=16.2 Hz, 1H), 3.45-3.31 (m, 2H), 2.42-2.34 (m, 1H), 2.19-2.10 (m, 1H), 1.44 (s, 9H). 13C NMR (151 MHz, CDCl$_3$) δ 165.9, 164.4, 156.2, 100.1, 79.9, 73.7, 36.3, 31.4, 28.5.

Polymer 22: Compound 21 (300 mg, 1.16 mmol) was placed in an oven dried flask. Sn(oct)$_2$ solution 0.3 M in THF (8.56 μL) was dripped in and the mixture was heated to 125° C. where compound 22 melted and was allowed to react for 1.25 hour. The polymer was purified by repeated precipitation into cold ether from a DCM solution to yield Polymer 22 (85.9 mg, 28.6%) as a colorless solid.

The molecular weight of polymer 22 was determined to be 4,000 Da, PDI=1.2 by gel-permeation chromatography (GPC) relative to PMMA standards. NMR analysis results were 1H NMR (600 MHz, CDCl$_3$) δ 5.25 (s, 1H), 5.05-4.66 (m, 3H), 3.43-3.18 (m, 2H), 2.23-2.01 (m, 2H), 1.43 (s, 9H).

Still referring to Scheme 4 (FIG. 8), compounds 23-25 and Polymer 26 were synthesized as follows:

Compound 23: Compound 5 (1.000 g. 5.7 mmol) was dissolved in THF (6 mL) in base washed glassware. The solution was chilled to 0° C. and a 1 M solution of borane in THF (8 mL) was added dropwise over 30 min. The reaction was allowed to warm to room temperature gradually and allowed to react for 3.5 hours. The reaction mixture was quenched with methanol at −78° C. and was concentrated. The reaction mixture was dissolved once more in methanol and concentrated then was dissolved in ethyl acetate and concentrated one more final time. The reaction mixture was dissolved in CH$_2$Cl$_2$ (8 mL) without purification. The solution was chilled to 0° C. and pyridine (1.401 mL, 17.4 mmol) was dripped in. A solution of TBDPSCl (3.188 g, 11.6 mmol) in CH$_2$Cl$_2$ (12 mL) was slowly dripped into the reaction mixture. The mixture was allowed to warm to room temperature and react for 14 hours after which is was quenched with distilled water, organic collected and aqueous extracted 2× more with CH$_2$Cl$_2$. Combined organic was washed with brine, dried over MgSO$_4$, and concentrated. The concentrated mixture was purified by silica column (Hexane/5% EtOAc) to yield compound 23 as colorless oil (1.364 g, 59.0%).

Using HRMS analysis, the composition of compound 23 was determined to be C$_{23}$H$_{30}$O$_4$SiNa. The measured mass was 421.1805; theoretical mass: 421.1806.

NMR analysis results were $^1$H NMR (600 MHz, CDCl$_3$) δ 7.70-7.64 (m, 4H), 7.46-7.35 (m, 6H), 4.64 (dd, J=8.4, 4.2 Hz, 1H), 3.92-3.87 (m, 1H), 3.82-3.75 (m, 1H), 2.20-2.12 (m, 1H), 1.96-1.88 (m, 1H), 1.59 (s, 3H), 1.55 (s, 3H), 1.05 (s, 9H). $^{13}$C NMR (151 MHz, CDCl$_3$) δ 173.8, 135.7, 135.7, 133.7, 133.6, 129.8, 129.8, 127.8, 127.8, 110.7, 71.0, 59.4, 34.7, 27.4, 26.9, 25.9.

Compound 24: Compound 23 (1.228 g, 3.1 mmol) was dissolved in 19 mL of THF, water, and AcOH 1:1:1. The reaction was stirred for 5 days. The reaction mixture was concentrated to yield compound 25 as a colorless oil (1.104 g, 73.2%) and was used directly to prepare compound 26.

Using HRMS analysis, the composition of compound 24 was determined to be C$_{20}$H$_{25}$O$_4$Si. Measured mass was 357.1530; theoretical mass was 357.1528.

Compound 25: Compound 24 (808 mg, 2.3 mmol) was dissolved in MeCN (16 mL) and chilled to 0° C. Et$_3$N (0.41 mL, 2.9 mmol) was dripped in followed by the dropwise addition of a solution of bromoacetyl bromide (0.25 mL, 2.9 mmol) in acetonitrile (5 mL). The reaction was stirred for 1.25 hour. The reaction was quenched with 1 M HCl, and extracted 3× with ethyl acetate. The combined organic was dried over MgSO$_4$ and concentrated. The resulting oil was used without further purification. The oil was dissolved in DMF (34 mL) and was dripped into a suspension of NaHCO$_3$ (0.284 g, 3.4 mmol) in DMF (68 mL) over a period of 28 hours. The reaction was stirred for a further 8 hours. The reaction mixture was concentrated, then suspended in ethyl acetate. The suspension was filtered and the filtrate was collected and concentrated. The resulting oil was purified by silica column (3:1 Hex/EtOAc) to yield compound 25 as colorless oil (0.137 g, 15.3%) over two steps.

NMR analysis results for compound 25 were $^1$H NMR (600 MHz, CDCl$_3$) δ 7.71-7.61 (m, 4H), 7.49-7.36 (m, 6H), 5.13 (dd, J=8.4, 4.8 Hz, 1H), 4.90 (d, J=16.8 Hz, 1H), 4.85 (d, J=16.8 Hz, 1H), 3.92-3.88 (m, 2H), 2.41-2.32 (m, 1H), 2.17-2.10 (m, 1H), 1.06 (s, 9H). $^{13}$C NMR (151 MHz, CDCl$_3$) δ 166.1, 164.2, 135.6, 135.6, 133.2, 133.1, 130.1, 128.0, 72.4, 65.3, 58.4, 33.9, 27.0, 19.3.

Polymer 26. Compound 25 (127 mg, 0.32 mmol) and compound 19 (17 mg, 0.04 mmol) were dissolved in CH$_2$Cl$_2$ (1 mL). 80 µL of 0.1 M methanol in CH$_2$Cl$_2$ was added dropwise to the reaction mixture. 80 µL of 0.1 M triazabicyclo[4.4.0]dec-5-ene in CH$_2$Cl$_2$ was added dropwise to the reaction mixture. The reaction was allowed to proceed for 15 hours. The polymer was purified by repeated precipitation into cold ether from a CH$_2$Cl$_2$ solution to yield Polymer 26 (62 mg, 48%) as a colorless solid.

The molecular weight of polymer 26 was determined to be 18,000 Da PDI=1.7 by gel-permeation chromatography (GPC) relative PMMA. NMR analysis results for polymer 26 were $^1$H NMR (600 MHz, CDCl$_3$) δ 7.66-7.58 (m, 4H), 7.42-7.30 (m, 6H), 5.49-5.41 (m, 1H), 4.84-4.70 (m, 1H), 4.64-4.50 (m, 1H), 3.81-3.65 (m, 2H), 2.34-2.23 (m, 1H), 2.11-1.95 (m, 1H), 1.05-0.97 (m, 9H).

We next sought to confirm that cyclizations driven by the pendant amine and alcohol nucleophiles contribute significantly to the degradation of polymers 16 and 17. While identifying small cyclic degradation products would be the most direct means of confirming the mechanism, polymers 16 and 17 are not compatible with such an approach. As small products are only formed when two adjacent protecting groups are removed, generating sufficient quantities of such products for detection by NMR requires removal of most protecting groups. Such thorough deprotection would require intense and lengthy irradiation that causes numerous side reactions. To circumvent these problems, we synthesized two model polymers with conventional protecting groups that could be completely removed by chemical means (Scheme 4). Using model polymers 22 and 26 the degradation products of these backbones were studied and the presence of significant quantities of cyclic compounds was confirmed.

Model polymer 22, analogous to polymer 16, was prepared with a Boc in place of the light-sensitive protecting group, by a method similar to that used for polymer 16. Boc protection of compound 1 yielded alcohol 20, which was acylated with bromoacetyl bromide and subsequently cyclized with sodium bicarbonate to yield dilactone 21. Monomer 21 proved difficult to polymerize, possibly due to an even stronger tendency towards transcarbamation than monomer 3. Using Sn(Oct)$_2$ as a catalyst instead of the previously used organic catalyst provided low molecular weight polymer 22 (4,000 Da; PDI=1.2).

The model polymer analogous to polymer 17, polymer 26, was prepared incorporating a silyl protecting group for the alcohol. Using methods adapted from the synthesis of polymer 17, compound 5 was reduced with borane, then protected with tert-butyl(chloro)diphenylsilane. The bulky protecting group was chosen to minimize deprotection of the silyl protecting group in the subsequent deprotection of ketal 23 with acetic acid to yield carboxylic acid 24. Carboxylic acid 24 was readily converted into dilactone monomer 25, using bromoacetyl bromide, which then was polymerized using the same technique as for the photosensitive polymers.

Figure 9A:
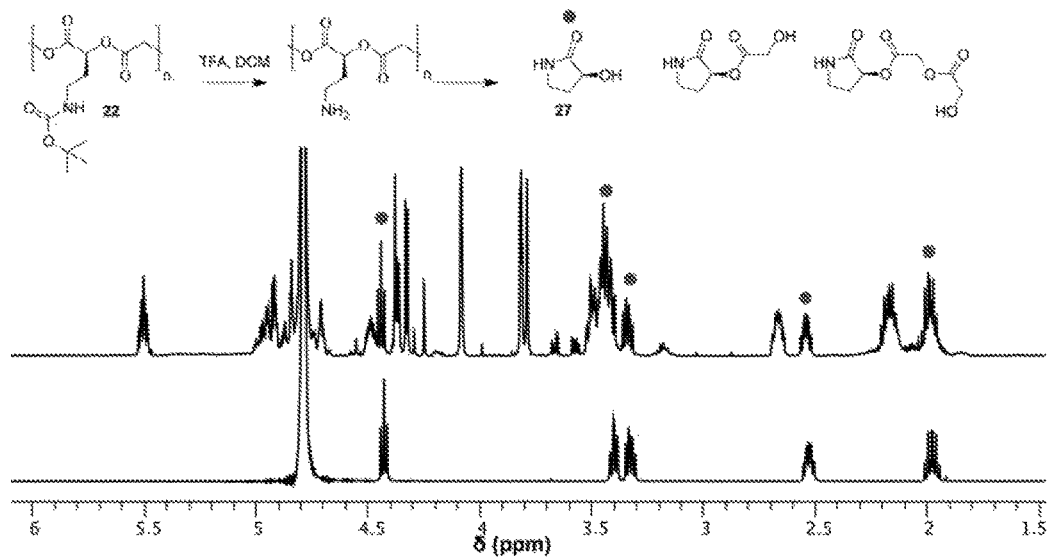
FIG. 9A shows deprotection and subsequent degradation of model polymer 22 to likely cyclic degradation products and $^1$H NMR spectra of degradation products of polymer 22 (upper) and compound 27 (lower)
Figure 9B:
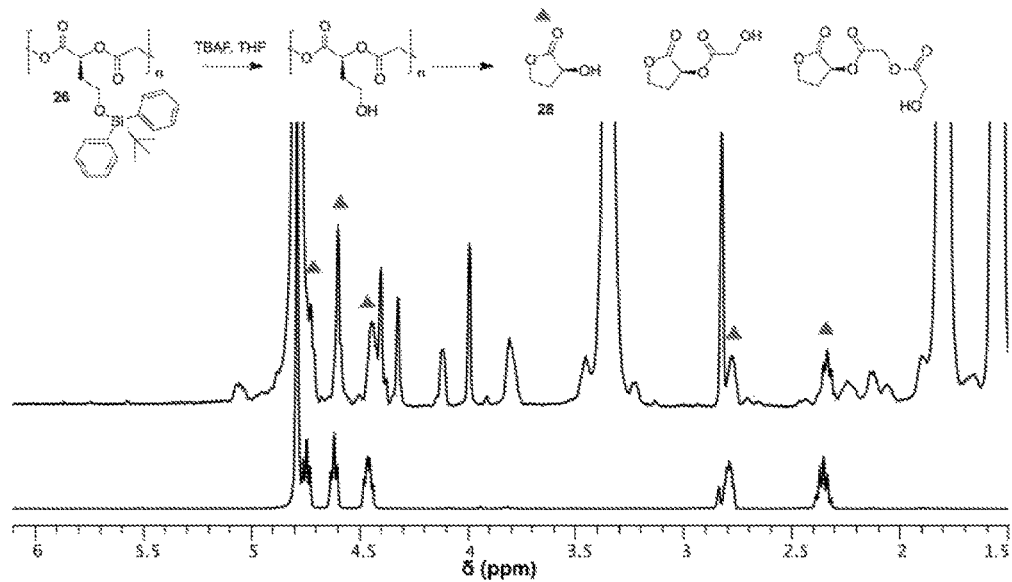
FIG. 9B shows deprotection and subsequent degradation of model polymer 26 to likely cyclic degradation products and $^1$H NMR spectra of degradation products of polymer 26 (upper) and compound 28 (lower).

To confirm the presence of cyclic degradation products for polymer 22 and polymer 26, they were deprotected with TFA or TBAF, respectively, and allowed to degrade. The deprotected materials were dissolved in deuterated buffer solutions prior to analysis by $^1$H NMR spectroscopy. Minimal changes occurred in the spectra over time, indicating that degradation had reached near completion before samples could be analyzed by $^1$H NMR spectroscopy, possibly during sample preparation or deprotection. Cyclic components were identified in the $^1$H NMR spectra by comparison to predicted product spectra. Due to the nature of the ROP, the glycolic acid and the α-hydroxyl acid with a pendant nucleophile do not alternate perfectly, though certain patterns should be more likely due to steric interactions. This means that degradation could yield multiple cyclic products (FIGS. 9A, 9B). The two most readily synthetically accessible predicted products are compounds 27 and 28. Compound 27 was prepared using a slightly modified method for a similar lactam, and compound 28 was readily obtained following a procedure developed by Denmark and Yang.

Scheme 5 shows the synthesis of model compound 27.

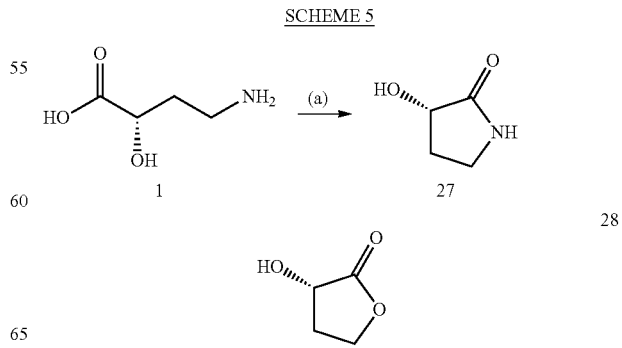

Compound 27: Compound 1 (1.0 g, 8.40 mmol) and alumina (2.57 g, 25.20 mmol) were suspended in toluene (43 mL) and heated to reflux with attached Dean-Stark apparatus. The reaction was allowed to proceed at reflux for 19 hours. The reaction was filtered and the solid washed with $CH_2Cl_2$. The filtrate was then collected and concentrated to yield compound 27 as colorless crystals (0.110 g, 12.9%).

Using HRMS analysis, the composition of compound 27 was determined to be $C_4H_7NO_2Na$. Measured mass was 124.0371; theoretical mass was 124.0369.

NMR analysis results for compound 27 were $^1H$ NMR (600 MHz, $CDCl_3$) δ 7.63 (bs, 1H), 5.35 (d, J=5.4 Hz, 1H), 4.02-3.95 (m, 1H), 3.18-3.12 (m, 1H), 3.11-3.04 (m, 1H), 2.28-2.21 (m, 1H), 1.79-1.69 (m, 1H). $^{13}C$ NMR (151 MHz, $CDCl_3$) δ 176.7, 68.4, 37.5, 30.5.

The peaks corresponding to these compounds were easily located in the degraded polymer spectra, confirming cyclization (FIGS. 9A, 9B). Peaks likely consistent with other cyclic products are also present in the degraded polymer spectra; the substantial difference between the methylene protons vicinal to the alcohol at 2-2.5 ppm is characteristic of those methylene protons when fixed in a ring. This evidence validates intramolecular cyclization as the major means of degradation for polymers of this backbone design upon deprotection.

FIG. 9A shows deprotection and subsequent degradation of model polymer 22 to likely cyclic degradation products and $^1H$ NMR spectra of degradation products of polymer 22 (upper trace) and compound 27 (lower trace). FIG. 9B shows deprotection and subsequent degradation of model polymer 26 to likely cyclic degradation products and $^1H$ NMR spectra of degradation products of polymer 26 (upper trace) and compound 28 (lower trace).

The three polymers were then formulated into nanoparticles to compare their degradation in a hydrophobic assembly and their potential for light-triggered release. Nanoparticles were formulated by single emulsion, both empty and encapsulating Nile red.

Figure 10A:
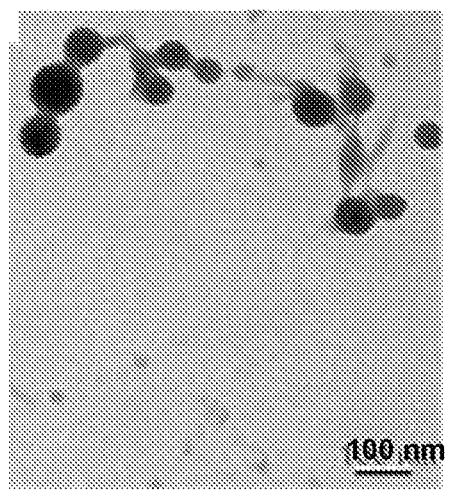
FIGS. 10A-10C are TEM micrographs of NP 16, NP 17, and NP 18, respectively. Scale bar=100 nm.
Figure 10B:
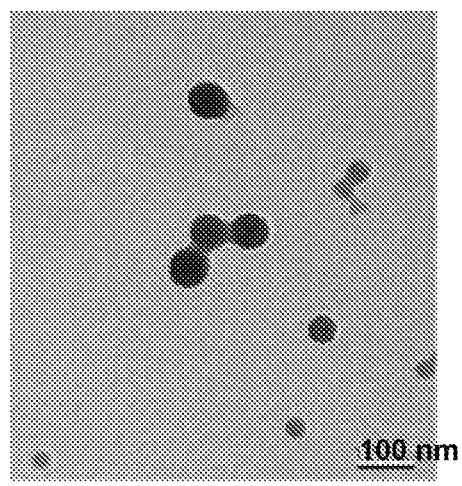
Figure 10C:
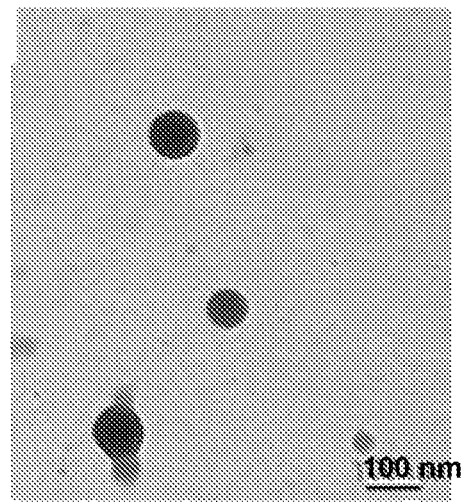

For formation of empty nanoparticles, 10 mg polymer was dissolved in 200 µL chloroform, which was then added to 8 mL of 3% PVA in water. The mixture was sonicated using a ⅛ inch tip sonicator (Misonix S-4000) at about 9.5 W for 5 min. Particle solution was stirred at room temperature for 1 hour, followed by rotavap at 40° C. to completely remove the organic solvent. The particle solution was then washed with Hyclone water by tangential flow filtration through 500 kDa Pellicon XL cassettes (Millipore). 100 mg of Trehalose was added to the particle solution, which was then frozen by liquid nitrogen and lyophilized. Particles were formulated from polymers 16, 17, 18 and PLGA to yield nanoparticles NP 16, NP 17, NP 18 and PLGA particles respectively. FIGS. 10A-10C are TEM micrographs of nanoparticles NP 16, NP 17, and NP 18, respectively. Scale bar=100 nm.

Nile red-loaded nanoparticles were formulated by dissolving 13 mg polymer in 200 µL dichloromethane and combined with 100 µL of Nile red solution in $CH_2Cl_2$ 0.13 mg/mL, which was then added to 6 mL of 1% PVA in water. The mixture was sonicated using a ⅛ inch tip sonicator (Misonix S-4000) at about 9.5 W for 5 min. Particle solution was stirred at room temp for 2 hours under light vacuum to completely remove the organic solvent. The particle solution was then washed with Hyclone water by tangential flow filtration through 500 kDa Pellicon XL cassettes (Millipore). 120 mg of Trehalose was added to the particle solution, which was then frozen by liquid nitrogen and lyophilized. Particles were formulated from polymers 16, 17, and 18 to yield nanoparticles NP-NR 16, NP-NR 17, and NP-NR 18 respectively.

To evaluate degradation, lyophilized particles were resuspended in 1×PBS (pH 7.4) at 50 µg/mL. 25 µL of the particle solution was added to 1 mL of 1×PBS (pH 7.4) in a UV-transparent cuvette (dimension: 12.5×12.5×45 mm). The particle solution was irradiated with a band-pass filter (320 to 390 nm) at 0.181 W/cm² for 15 sec. DLS was used to monitor the size, PDI and count rate continuously immediately after irradiation.

Degradation of polymers 16, 17, and 18 measured was by GPC. The GPC traces for each polymer are shown in FIGS. 6A-C, 7A-C. The polymer was dissolved in a mixture of acetonitrile and PBS (1×) 90:10 at a 0.2 mg/mL concentration. Irradiated samples were irradiated in a Luzchem photoreactor for 15 min (1 mW/cm2). The samples were incubated at 37° C. for the specified times, i.e., 30 min., 1 hour, 4 hours, 23 hours, and 48 hours. At the given times, the samples were concentrated at 30° C., dissolved in DMF with 0.01% LiBr, and analyzed by gel permeation chromatography monitoring at 320 nm.

Figure 11A:
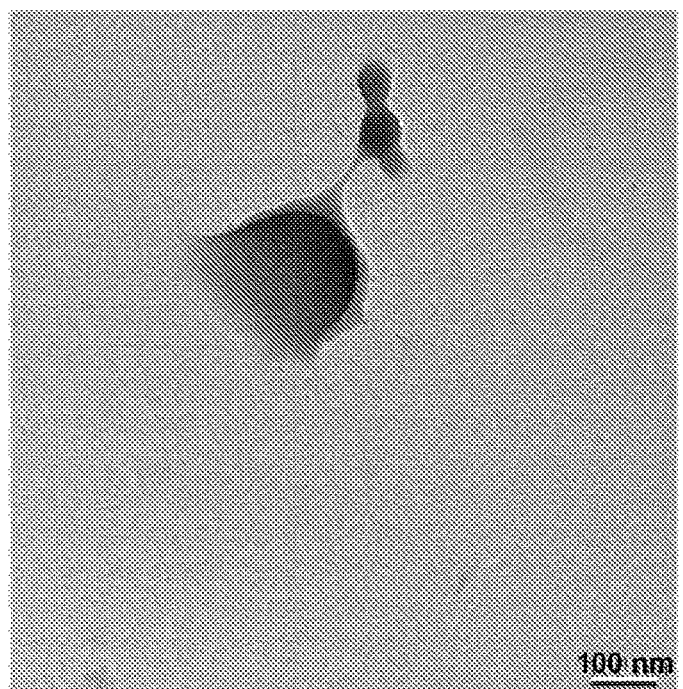
FIG. 11A is a TEM micrograph of NP 16 after irradiation at 320-390 nm (0.181 W/cm$^2$) for 15 sec and overnight incubation at 37° C. (scale bar=100 nm)
Figure 11B:
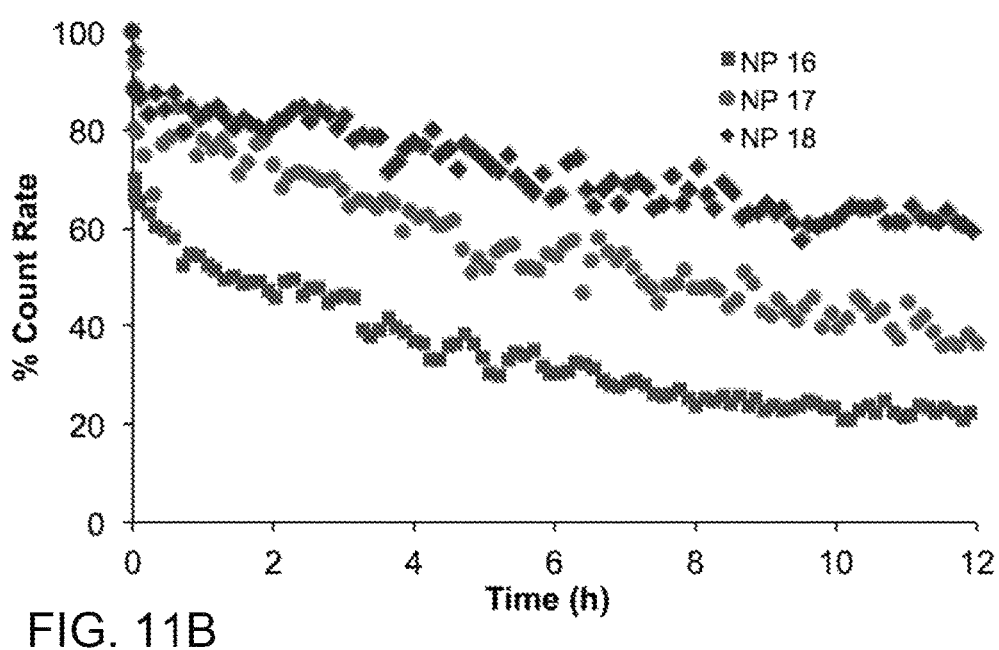
FIG. 11B is a plot of the DLS count rate of NP 16, NP 17 and NP 18 irradiated at 320-390 nm (0.181 W/cm$^2$) for 15 s and incubated at room temperature in 1×PBS (pH 7.4)
Figure 11C:
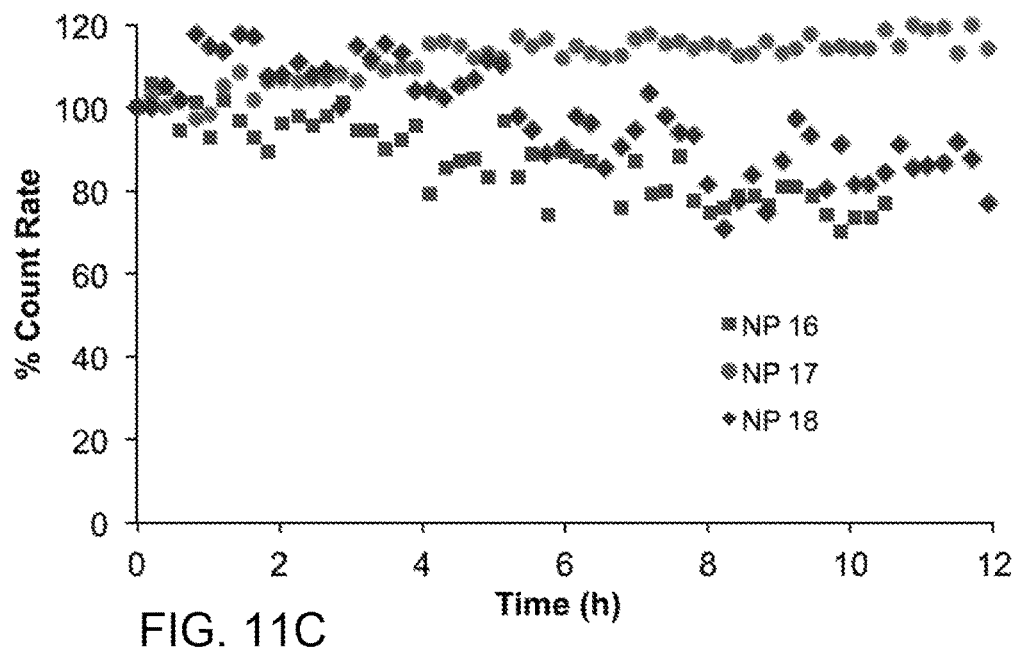
FIG. 11C plots the results for non-irradiated NP 16, NP 17 and NP 18 incubated at room temperature in 1×PBS (pH 7.4)
Figure 11D:
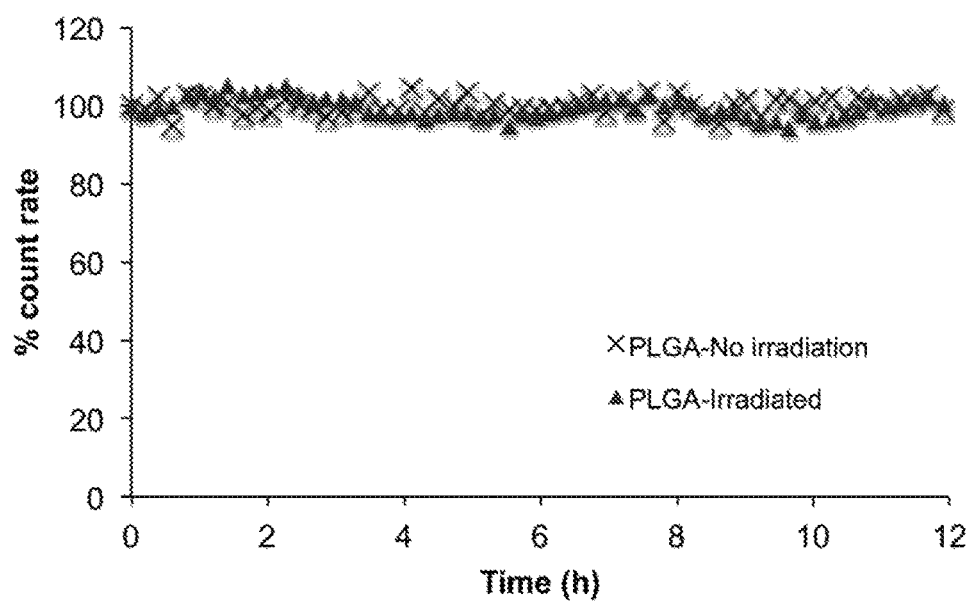
FIG. 11D plots the DLS count rate for PLGA particles irradiated with the above conditions and not irradiated incubated at room temperature in 1×PBS (pH 7.4).
Figure 12A:
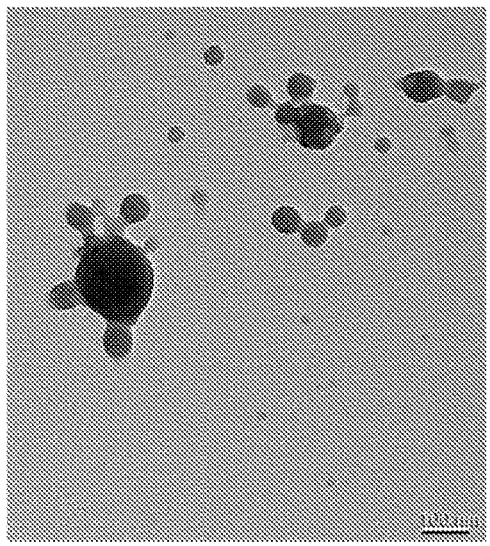
FIGS. 12A and 12B are TEM micrographs of NP 17 following irradiation.
Figure 12B:
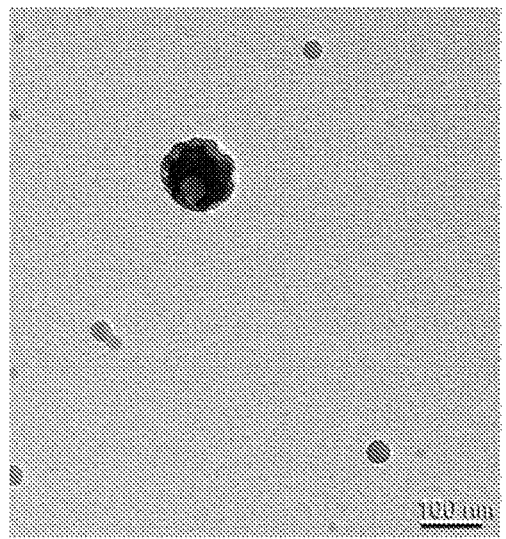
Figure 12C:
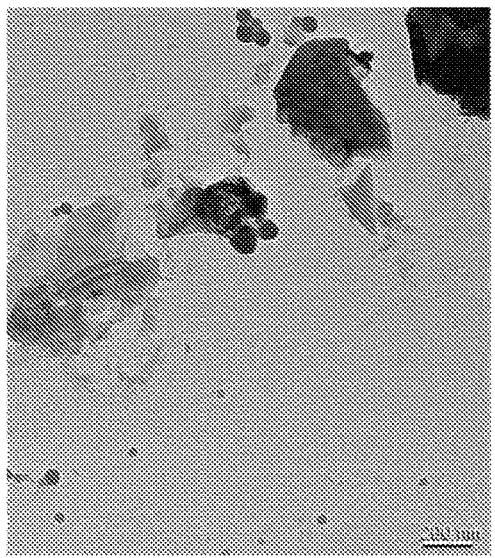
FIGS. 12C and 12D show NP 18 after irradiation.
Figure 12D:
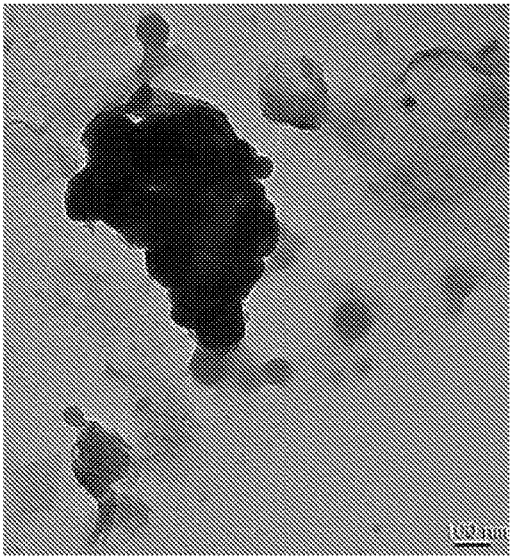

The degradation of empty particles was continuously monitored by DLS following irradiation for 15 sec (0.181 W/cm²) (FIG. 11B). The count rate for irradiated particles of polymer 16 decreased more rapidly than for other particles. This rapid degradation likely results from the major increase in hydrophilicity upon release of the amine, as well as the amine's high nucleophilicity allowing rapid intramolecular cyclization. Particles of polymer 17, NP 17, also rapidly degrade. The count rate of irradiated particles of polymer 18 decreased at a rate similar to non-irradiated NP 18 (FIG. 11C). Particles formulated with PLGA behaved identically when irradiated and not irradiated under these conditions (FIG. 11D). To confirm NP degradation, transmission electron microscopy (TEM) micrographs of irradiated and non-irradiated particles were also obtained. In agreement with the DLS data, particle densities of NP 16 and NP 17 were markedly lower after irradiation 15 sec (0.181 W/cm²) and overnight incubation (e.g., 24 and 48 hours) at 37° C. After irradiation, NP 16 (FIG. 11A) and NP 17 (FIGS. 12A, 12B) also contained substantial quantities of aggregates with no clear spherical structure, likely material from degraded particles. Irradiated NP 18 (FIGS. 12C, 12D) still had substantial numbers of intact particles, though the particles did appear to exhibit increased aggregation following irradiation.

Figure 13A:
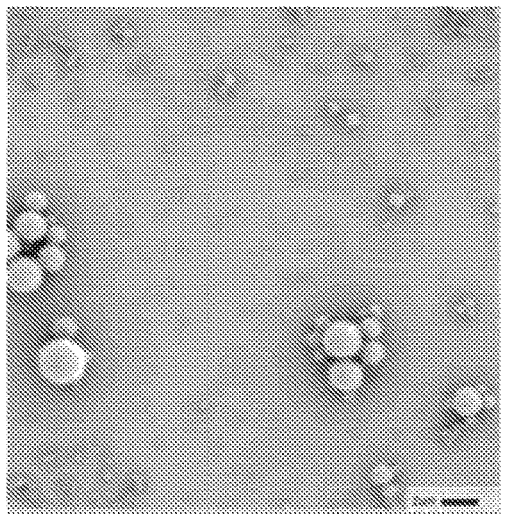
FIGS. 13A-C are SEM images of nanoparticles NP 16, NP 17 and NP 18, respectively, each encapsulating Nile red.
Figure 13B:
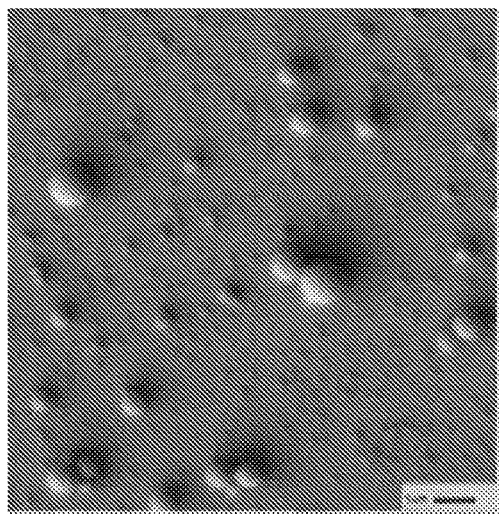
Figure 13C:
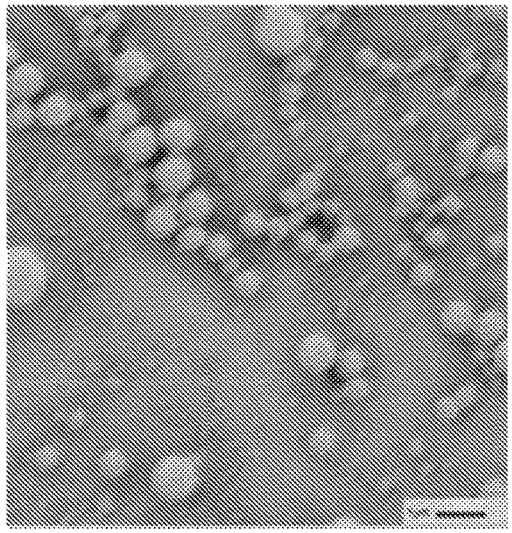
Figure 14A:
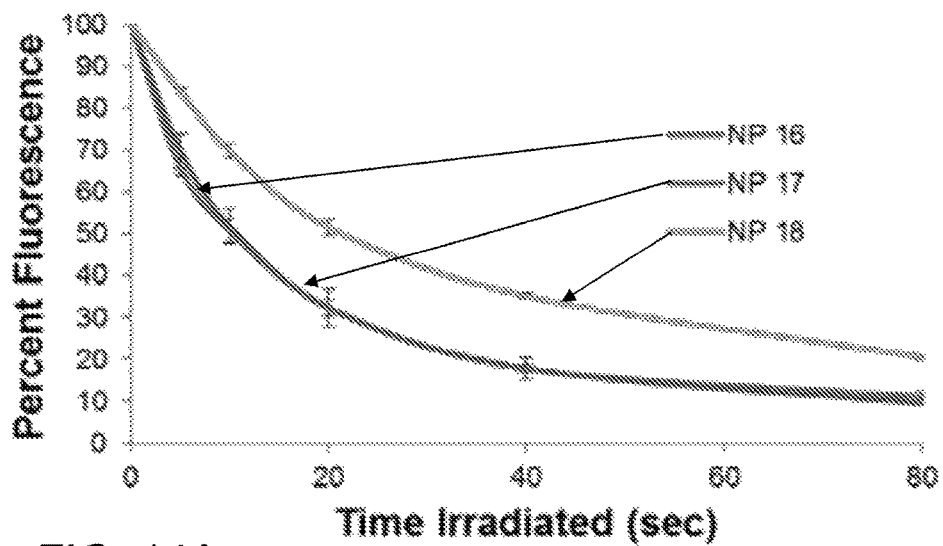
FIGS. 14A and 14B are plots showing fluorescence quenching of Nile red encapsulated polymeric nanoparticles, irradiated with UV light (1 mW/cm$^2$) and non-irradiated with incubation at 37° C., respectively.
Figure 14B:
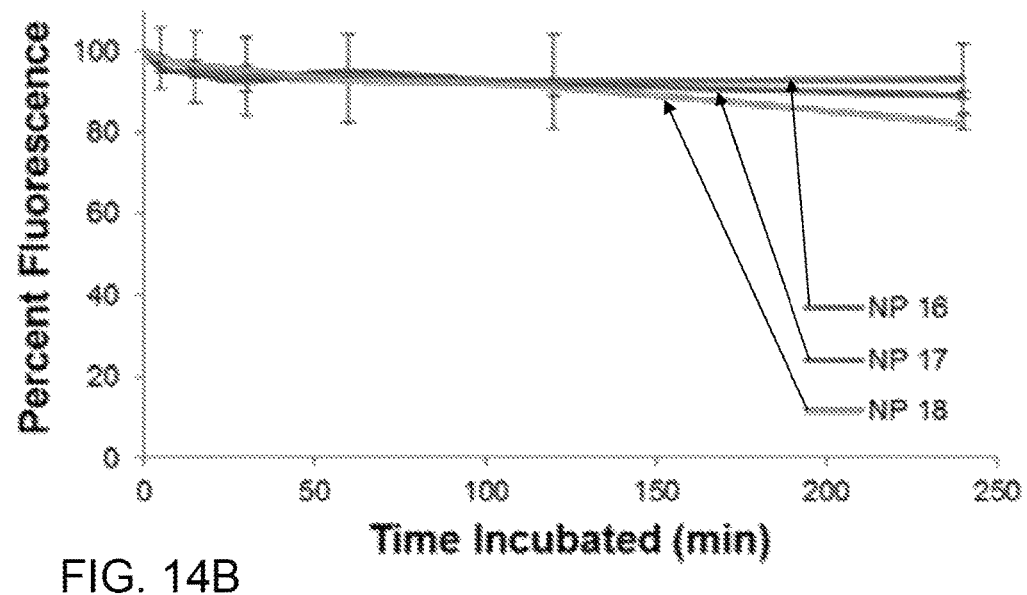

To assess utility for triggered release, particles were also formulated encapsulating the fluorescent dye Nile red (NP-NR). Nile red is fluorescent in hydrophobic environments, like that of a hydrophobic nanoparticle, and is quenched by water. FIGS. 13A-13C are SEM images of particles encapsulating Nile red, where FIG. 13A shows NP 16, FIG. 13B shows NP 17, and FIG. 13C shows NP 18 formulated by single emulsion. Upon irradiation with UV light (1 mW/cm²), Nile red fluorescence was rapidly quenched in all three particles, but most quickly in NP-NR 16 and NP-NR 17, which are composed of the polymers that degrade rapidly through cyclization (FIG. 14A). Rapid quenching is indicative of substantial structural changes to the particles, allowing both release of Nile red and water influx. Particles are stable over at least four hours when not irradiated (FIG. 14B).

Disclosed herein are novel polymers with a poly(lactide-co-glycolide)-type backbone that contain pendant protected nucleophiles. In polymers containing pendant alcohols or amines, polymer degradation following deprotection is accelerated by intramolecular cyclization events that cause breaks in the polymer backbone. This backbone has the potential to support a variety of protecting groups sensitive to different triggers.

REFERENCES (INCORPORATED HEREIN BY REFERENCE)

(1) Dong, H. D.; Esser-Kahn, A. P.; Thakre, P. R.; Patrick, J. F.; Sottos, N. R.; White, S. R.; Moore, J. S. *Acs Appl Mater Inter* 2012, 4, 503.
(2) Nie, Z. H.; Kumacheva, E. *Nat Mater* 2008, 7, 277.
(3) Vozzi, G.; Flaim, C.; Ahluwalia, A.; Bhatia, S. *Biomaterials* 2003, 24, 2533.
(4) Lu, Y.; Chen, S. C. *Adv Drug Deliver Rev* 2004, 56, 1621.
(5) Nair, L. S.; Laurencin, C. T. *Prog Polym Sci* 2007, 32, 762.
(6) Vauthier, C.; Dubernet, C.; Fattal, E.; Pinto-Alphandary, H.; Couvreur, P. *Adv Drug Deliver Rev* 2003, 55, 519.
(7) Cheng, R.; Meng, F. H.; Deng, C.; Klok, H. A.; Zhong, Z. Y. *Biomaterials* 2013, 34, 3647.
(8) Jain, R. A. *Biomaterials* 2000, 21, 2475.
(9) Athanasiou, K. A.; Niederauer, G. G.; Agrawal, C. M. *Biomaterials* 1996, 17, 93.
(10) Woodruff, M. A.; Hutmacher, D. W. *Prog Polym Sci* 2010, 35, 1217.
(11) de Gracia Lux, C.; Olejniczak, J.; Fomina, N.; Viger, M. L.; Almutairi, A. *Journal of Polymer Science* Part A: Polymer Chemistry 2013, 51, 3783.
(12) Mejia, J. S.; Gillies, E. R. *Polym Chem-Uk* 2013, 4, 1969.
(13) Lux, C. D.; Almutairi, A. *ACS macro letters* 2013, 2, 432.
(14) Lv, A.; Li, Z. L.; Du, F. S.; Li, Z. C. *Macromolecules* 2014, 47, 7707.
(15) Park, T. G. *Biomaterials* 1995, 16, 1123.
(16) Panyam, J.; Labhasetwar, V. *Adv Drug Deliver Rev* 2003, 55, 329.
(17) C. G. Pitt, M. M. G., G. L. Kimmel, J. Surles and A. Schindler *Biomaterials* 1981, 2, 215.
(18) Patchorn. A; Amit, B.; Woodward, R. B. *J Am Chem Soc* 1970, 92, 6333.
(19) Blanc, A.; Bochet, C. G. *J Am Chem Soc* 2004, 126, 7174.
(20) Klinger, D.; Landfester, K. *Macromolecules* 2011, 44, 9758.
(21) Osornio, Y. M.; Uebelhart, P.; Bosshard, S.; Konrad, F.; Siegel, J. S.; Landau, E. M. *J Org Chem* 2012, 77, 10583.
(22) Yin, L. C.; Tang, H. Y.; Kim, K. H.; Zheng, N.; Song, Z. Y.; Gabrielson, N. P.; Lu, H.; Cheng, J. *J. Angew Chem Int Edit* 2013, 52, 9182.
(23) Azagarsamy, M. A.; Anseth, K. S. *Angew Chem Int Edit* 2013, 52, 13803.
(24) Griffin, D. R.; Schlosser, J. L.; Lam, S. F.; Nguyen, T. H.; Maynard, H. D.; Kasko, A. M. *Biomacromolecules* 2013, 14, 1199.
(25) Stanton-Humphreys, M. N.; Taylor, R. D. T.; McDougall, C.; Hart, M. L.; Brown, C. T. A.; Emptage, N. J.; Conway, S. *J. Chem Commun* 2012, 48, 657.
(26) Gu, Z.; Biswas, A.; Joo, K. I.; Hu, B. L.; Wang, P.; Tang, Y. *Chem Commun* 2010, 46, 6467.
(27) Kostiainen, M. A.; Smith, D. K.; Ikkala, O. *Angew Chem Int Edit* 2007, 46, 7600.
(28) Griffin, D. R.; Kasko, A. M. *J Am Chem Soc* 2012, 134, 17833.
(29) DeForest, C. A.; Anseth, K. S. *Nat Chem* 2011, 3, 925.
(30) Yu, Y.; Zou, J.; Cheng, C. *Polym Chem-Uk* 2014, 5, 5854.
(31) Pounder, R. J.; Dove, A. P. *Polym Chem-Uk* 2010, 1, 260.
(32) Pounder, R. J.; Dove, A. P. *Biomacromolecules* 2010, 11, 1930.
(33) Levy, D. E.; Lapierre, F.; Liang, W. S.; Ye, W. Q.; Lange, C. W.; Li, X. Y.; Grobelny, D.; Casabonne, M.; Tyrrell, D.; Holme, K.; Nadzan, A.; Galardy, R. E. *J Med Chem* 1998, 41, 199.
(34) Dove, A. P. *ACS macro letters* 2012, 1, 1409.
(35) Kamber, N. E.; Jeong, W.; Waymouth, R. M.; Pratt, R. C.; Lohmeijer, B. G. G.; Hedrick, J. L. *Chem Rev* 2007, 107, 5813.
(36) Kiesewetter, M. K.; Shin, E. J.; Hedrick, J. L.; Waymouth, R. M. *Macromolecules* 2010, 43, 2093.
(37) Pratt, R. C.; Lohmeijer, B. G. G.; Long, D. A.; Waymouth, R. M.; Hedrick, J. L. *J Am Chem Soc* 2006, 128, 4556.
(38) Aujard, I.; Benbrahim, C.; Gouget, M.; Ruel, O.; Baudin, J. B.; Neveu, P.; Jullien, L. *Chem-Eur J* 2006, 12, 6865.
(39) Pathak, T.; Thomas, N. F.; Akhtar, M.; Gani, D. *Tetrahedron* 1990, 46, 1733.
(40) Denmark, S. E.; Yang, S. M. *J Am Chem Soc* 2004, 126, 12432.

The invention claimed is:
1. A composition comprising a polymer having a poly(lactide-co-glycolide) backbone and pendant nucleophiles protected by a stimulus-responsive protecting group, wherein the polymer comprises

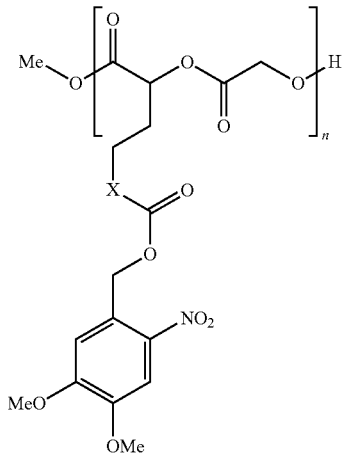

or a derivative thereof, where X is NH, O or S, and wherein the protecting group is configured to deprotect upon exposure to a stimulus to facilitate degradation by intramolecular cyclization.
2. The composition of claim 1, wherein the protecting group is photocleavable and the stimulus is light.
3. The composition of claim 2, wherein the light is UV light.
4. The composition of claim 1, wherein the protecting group is an ortho-nitrobenzyl (ONB) protecting group.
5. The composition of claim 1, wherein the polymer degrades according to:

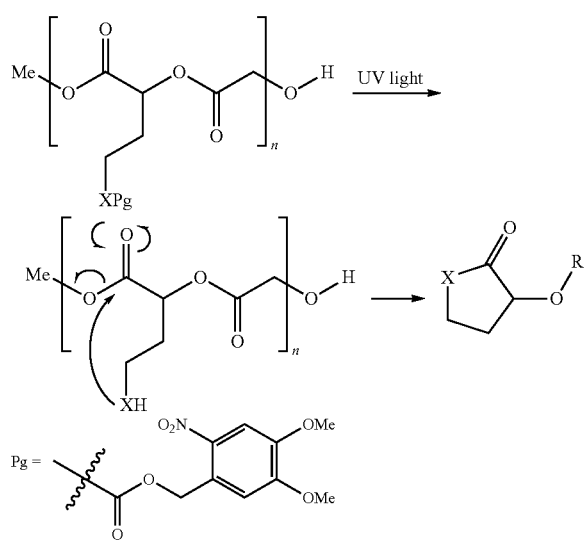

where X is NH, O or S.

6. The composition of claim 1, wherein the polymer is configured as a plurality of nanoparticles, the composition further comprising a payload encapsulated within each nanoparticle.

7. The composition of claim 6, wherein the payload is selected from the group consisting of imaging agents, bioactive agents, and pharmaceutical agents.

8. The composition of claim 1, wherein the pendant nucleophile is an amine.

9. The composition of claim 1, wherein the pendant nucleophile is an alcohol.

10. The composition of claim 1, wherein the pendant nucleophile is a thiol.

11. A composition comprising a polymer comprising:
a polymer backbone comprising a poly(lactide-co-glycolide) comprising

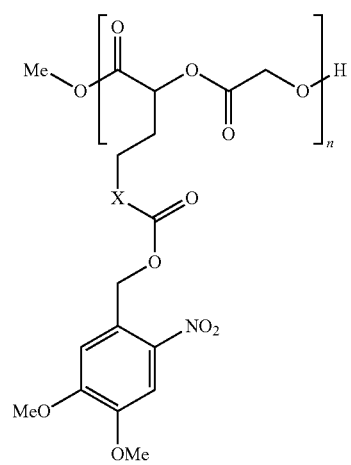

or a derivative thereof, where X is NH, O or S, and;
pendant nucleophiles linked to the backbone and protected by a photolabile protecting group, wherein the protecting group is configured to deprotect upon exposure to irradiation to facilitate degradation of the nucleophiles to five membered rings by intramolecular cyclization.

12. The composition of claim 11, wherein the irradiation is UV light.

13. The composition of claim 11, wherein the protecting group is an ortho-nitrobenzyl (ONB) protecting group.

14. The composition of claim 11, wherein the polymer degrades according to:

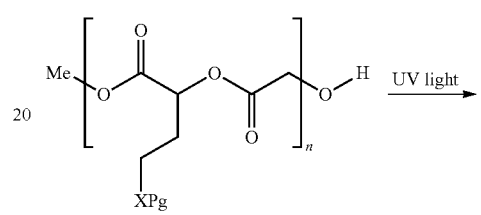

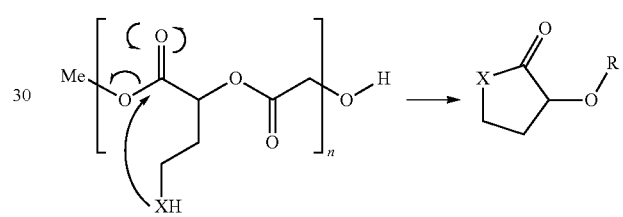

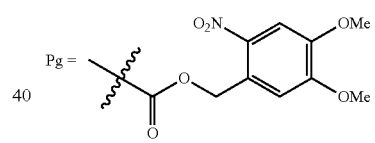

where X is NH, O or S.

15. The composition of claim 11, wherein the polymer is configured as a plurality of nanoparticles, the composition further comprising a payload encapsulated within each nanoparticle.

16. The composition of claim 15, wherein the payload is selected from the group consisting of imaging agents, bioactive agents, and pharmaceutical agents.

17. The composition of claim 11, wherein the pendant nucleophile is an amine.

18. The composition of claim 11, wherein the pendant nucleophile is an alcohol.

19. The composition of claim 11, wherein the pendant nucleophile is a thiol.

* * * * *